United States Patent
Sasaki et al.

(10) Patent No.: US 6,593,364 B2
(45) Date of Patent: Jul. 15, 2003

(54) TRITERPENE DERIVATIVES AND REMEDIES FOR LIVER DISEASES

(75) Inventors: Kazue Sasaki, Yokohama (JP); Nobuto Minowa, Yokohama (JP); Shoji Nishiyama, Yokohama (JP); Hiroyuki Kuzuhara, Yokohama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/921,983

(22) Filed: Aug. 6, 2001

(65) Prior Publication Data

US 2002/0016481 A1 Feb. 7, 2002

Related U.S. Application Data

(62) Division of application No. 09/536,631, filed on Mar. 28, 2000, now abandoned, which is a division of application No. 09/125,776, filed as application No. PCT/JP97/00555 on Feb. 26, 1997, now Pat. No. 6,201,018.

(30) Foreign Application Priority Data

Feb. 26, 1996 (JP) .............................................. 8-37829

(51) Int. Cl.[7] ..................... A61K 31/215; A61K 31/255; A61K 31/335; A61K 31/045
(52) U.S. Cl. ..................... 514/529; 514/453; 514/517; 514/700; 514/729; 514/893; 514/894
(58) Field of Search .................... 568/823; 514/700, 514/893, 894, 529, 517, 729, 453

(56) References Cited

U.S. PATENT DOCUMENTS

| | | | |
|---|---|---|---|
| 5,064,823 A | * 11/1991 | Lee et al. | ..................... 514/198 |
| 5,314,877 A | 5/1994 | Suzuki et al. | |
| 5,650,167 A | 7/1997 | Allison | |
| 5,723,149 A | * 3/1998 | Bonte et al. | ................. 424/450 |

FOREIGN PATENT DOCUMENTS

| | | | |
|---|---|---|---|
| JP | 61-85344 | | 4/1986 |
| WO | WO92/09262 | | 6/1992 |
| WO | WO 92/09262 | * | 6/1992 |
| WO | WO97/03088 | | 1/1997 |

OTHER PUBLICATIONS

Okubo et al., *Biosci. Biotech. Biochem.*, vol. 56(1), pp. 99–103, 1992.*
Chiang et al., *Journal of Medicinal Plant Research*, vol. 46, pp. 52–55, 1982.*
Chiang et al., *Journal of Medicinal Plant Research*, vol. 46, pp. 52–55 (1982).
Kitagawa et al., *Chem. Pharm. Bull.*, vol. 24, No. 1, pp. 121–129 (1976).
J. Kinjo et al., *Food Factors Cancer Prev., Int. Conf.*, 323–327 (meeting date 1995, published 1997).
H. Ohminami et al., *Planta Med.*, 6, 440–441 (1984).
A. Seawright et al., *Australian Veterinary Journal*, 53 (May 1977).
M. Pass et al., *Toxicology and Applied Pharmacology*, 51, 515–521 (May 1977).
Kitagawa et al., *Chem. Pharm. Bull.*, 36(1), pp. 153–161 (1988).
Okubo et al., *Biosci. Biotech. Biochem.*, 56(1), pp. 99–103 (1992).

* cited by examiner

*Primary Examiner*—Barbara P. Badio
(74) *Attorney, Agent, or Firm*—Wenderoth, Lind & Ponack, L.L.P.

(57) ABSTRACT

A triterpene derivative useful for the treatment of hepatic disorders is disclosed. This compound comprises as an active ingredient a triterpene derivative represented by the following formula (I) or a salt thereof:

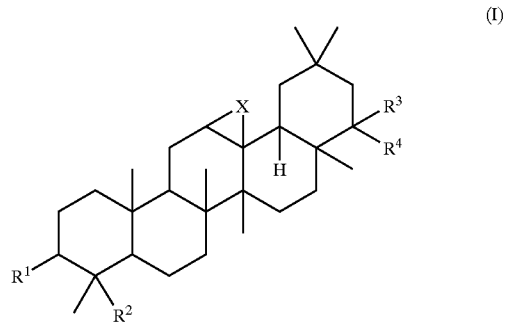

wherein $R^1$ represents a hydroxyl group, arylmethyloxy, lower alkoxy, or lower alkanoyloxy, $R^2$ represents lower alkyl, lower alkenyl, —$CH_2OR^5$, formyl, —$COOR^6$, or —$CH_2N(R^7)R^8$, or $R^1$ and $R^2$ may combine with each other to form —O—$C(R^9)R^{10}$—O—$CH_2$—, $R^3$ and $R^4$, which may be the same or different represent a hydrogen atom, a hydroxyl group, lower alkyl, lower alkenyl, aryl, hydroxymethyl, —$N(R^{11})R^{12}$, formyl, —$COOR^6$, or —$OR^{13}$, or $R^3$ and $R^4$ may combine with each other to form oxo, hydroxyimino, or alkylidene and X represents O, $CH_2$, or NH.

7 Claims, 1 Drawing Sheet

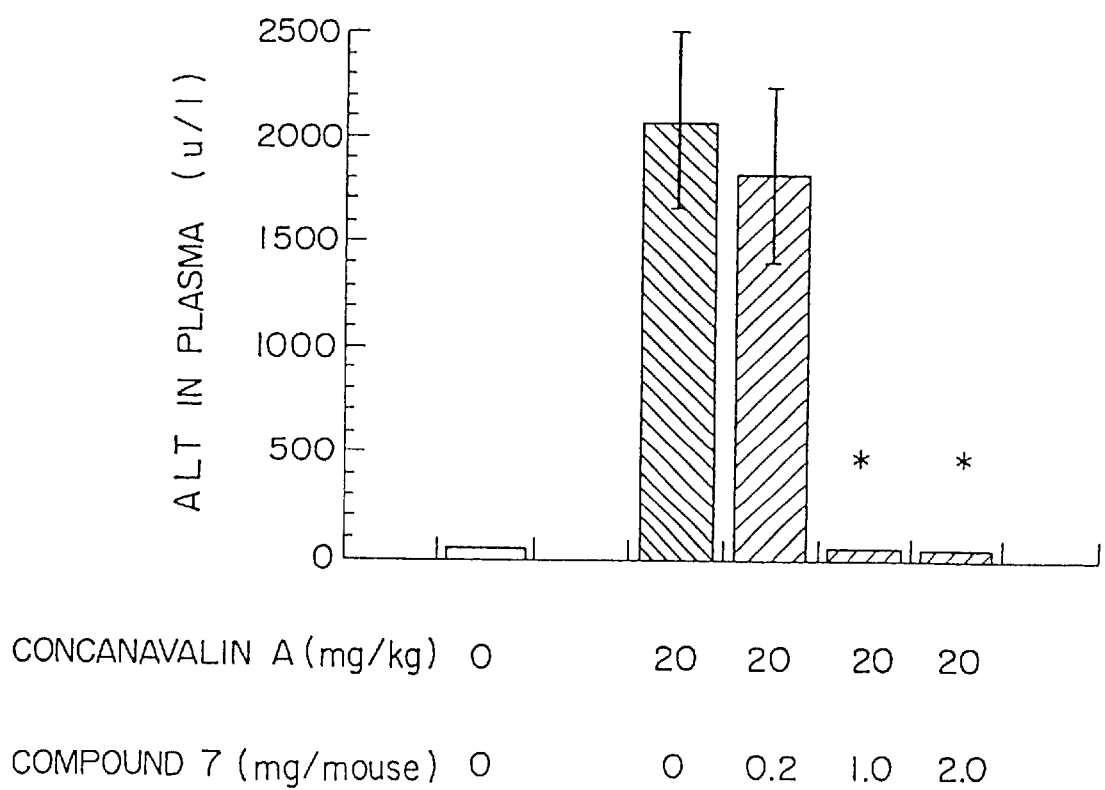
F I G. 1

TRITERPENE DERIVATIVES AND REMEDIES FOR LIVER DISEASES

This is a divisional of Ser. No. 09/536,631, filed Mar. 28, 2000, now abandoned, which is a divisional of Ser. No. 09/125,776, filed Aug. 26, 1998, now U.S. Pat. No. 6,201,018, which is a 371 of PCT/JP97/00555 filed Feb. 26, 1997.

BACKGROUND OF THE INVENTION

1. Field of the Invention

The present invention relates to pharmaceutical compositions, for hepatic disorders, comprising triterpene derivatives or salts thereof as an active ingredient. The present invention also relates to novel triterpene derivatives.

2. Background Art

A liver is an important organ which has various functions necessary for maintaining life of a living body, such as detoxication, various metabolisms, and storage of substances. It, however, often undergoes acute or chronic damage due to viruses, drugs, alcohols and other various causes. This induces viral hepatitis, drug-induced hepatopathy, alcoholic hepatopathy, fatty liver, and, in addition, diseases such as cirrhosis and hepatic cancer.

For treating such hepatic diseases, alimentary therapy, rest cure, and other therapies using glycyrrhizin preparations, adrenocortical steroids, interferon and the like have hitherto been employed. These therapies, however, cannot be said to be satisfactorily effective for the treatment of hepatic disorders. Glycyrrhizin and interferon are intravenously administered and, hence, unsuitable for prolonged administration. Further, the interferon and steroids have a problem of side effect.

Some triterpene derivatives have anticomplementary activity and platelet aggregation inhibitory activity. Thus, they and are known as prophylactic and pharmaceutical compositions for immunological diseases and thrombosis (Japanese Patent Laid-Open No. 85344/1986). However, there is no report which discloses that the triterpene derivatives are effective as a pharmaceutical composition for treating hepatic disorders.

SUMMARY OF THE INVENTION

The present inventors have now found that certain triterpene derivatives are effective for treating hepatic disorders. Further, they have succeeded in synthesis of novel triterpene derivatives. The present invention has been made based on such novel finding.

According to the first aspect of the present invention, there is provided a pharmaceutical composition for treating a hepatic disorder comprising as an active ingredient a triterpene derivative represented by the following formula (I) or a salt thereof:

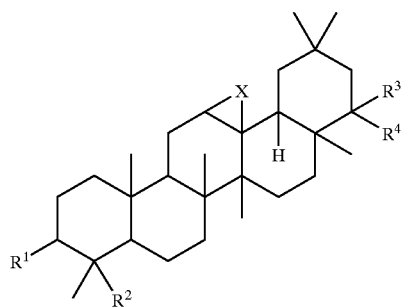

(I)

wherein
$R^1$ represents
a hydroxyl group,
arylmethyl oxy,
lower alkoxy, or
lower alkanoyloxy;
$R^2$ represents
lower alkyl,
lower alkenyl,
—$CH_2OR^5$ wherein $R^5$ represents a hydrogen atom, arylmethyl, lower alkyl, or lower alkanoyl,
formyl,
—$COOR^6$ wherein $R^6$ represents a hydrogen atom or lower alkyl, or
—$CH_2N(R^7)R^8$ wherein $R^7$ and $R^8$, which may be the same or different, represent a hydrogen atom, lower alkyl, aryl, or lower alkanoyl;
or $R^1$ and $R^2$ may combine with each other to form —O—$C(R^9)R^{10}$—O—$CH_2$— wherein $R^9$ and $R^{10}$, which may be the same or different, represent a hydrogen atom, lower alkyl, or aryl;
$R^3$ and $R^4$, which may be the same or different, represent
a hydrogen atom,
a hydroxyl group,
lower alkyl,
lower alkenyl,
aryl,
hydroxymethyl,
—$N(R^{11})R^{12}$ wherein $R^{11}$ and $R^{12}$, which may be the same or different, represent a hydrogen atom, lower alkyl, or lower alkanoyl,
formyl,
—$COOR^6$ wherein $R^6$ is as defined above,
—$OR^{13}$ wherein $R^{13}$ represents lower alkyl, cyclo-lower alkyl, aralkyl, lower alkanoyl, arylcarbonyl, aralkylcarbonyl, lower alkenyl, lower alkenylcarbonyl, or aryl-lower alkenylcarbonyl;
or $R^3$ and $R^4$ may combine with each other to form oxo, hydroxyimino, or alkylidene; and
X represents O, $CH_2$, or NH.

According to the second aspect of the present invention, there is provided a pharmaceutical composition for treating a hepatic disorder, comprising as an active ingredient a triterpene derivative represented by the following formula (II) or a salt thereof:

(II)

wherein
$R^{16}$ represents
a hydroxyl group,
arylmethyloxy,
lower alkoxy, or
lower alkanoyloxy;

$R^{17}$ represents lower alkyl, lower alkenyl

—$CH_2OR^5$ wherein $R^5$ is as defined above, formyl,

—$COOR^6$ wherein $R^6$ is as defined above,

—$CH_2OCON(R^9)R^{10}$ wherein $R^9$ and $R^{10}$ are as defined above,

—$CON(R^{29})R^{30}$ wherein $R^{29}$ and $R^{30}$, which may be the same or different, represent a hydrogen atom, lower alkyl, lower alkanoyl, aryl, or aralkyl;

—$CH_2N(R^7)R^8$ wherein $R^7$ and $R^8$ are as defined above;

—$C(R^6)_2OH$ wherein $R^6$ is as defined above;

—$COR^6$ wherein $R^6$ is as defined above;

—$CH=CHR^6$ wherein $R^6$ is as defined above;

or $R^{16}$ and $R^{17}$ may combine with each other to form —O—$C(R^9)R^{10}$—O—$CH_2$— wherein $R^9$ and $R^{10}$ are as defined above;

$R^{18}$ and $R^{19}$, which may be the same or different, represent a hydrogen atom, a hydroxyl group, arylmethyloxy, lower alkyl, —$N(R^{11})R^{12}$ wherein $R^{11}$ and $R^{12}$ are as defined above, —$COOR^6$ wherein $R^6$ is as defined above, —$OR^{13}$ wherein $R^{13}$ is as defined above, —O—$(CH_2)_m$—$R^{22}$ wherein $R^{22}$ represents amino, —NH—$COOR^{23}$ wherein $R^{23}$ represents arylmethyl or lower alkyl, a hydroxyl group, arylmethyloxy, or —$COOR^{24}$ wherein $R^{24}$ represents a hydrogen atom, lower alkyl, or arylmethyl, and m is an integer of 1 to 4, —$OCOCH(R^{25})(CH_2)_n$—$R^{22}$ wherein $R^{22}$ is as defined above, $R^{25}$ represents a hydrogen atom, lower alkyl, aralkyl, or aryl, and n is an integer of 0 to 3, —$OCOCH=CH$—$COOR^6$ wherein $R^6$ is as defined above, or —$OCON(R^{29})R^{30}$ wherein $R^{29}$ and $R^{30}$ are as defined above;

or $R^{18}$ and $R^{19}$ may combine with each other to form oxo, $R^{20}$ and $R^{21}$ respectively represent the same meanings as $R^{18}$ and $R^{19}$, provided that $R^{20}$ and $R^{21}$ do not represent a hydrogen atom;

or $R^{18}$ and $R^{20}$ may combine with each other to form —O—$[C(R^9)R^{10}]_p$—O— wherein $R^9$ and $R^{10}$ are as defined above and p is an integer of 1 to 3, or —OCO—$[C(R^9)R^{10}]_q$—OCO— wherein $R^9$ and $R^{10}$ are as defined above and q is an integer of 0 to 2; and Y represents O, $CH_2$, NH, or a single bond to form a double bond in the ring with Y bonded thereto.

According to the third aspect of the present invention, there is provided a pharmaceutical composition for treating a hepatic disorder, comprising as an active ingredient a triterpene derivative represented by the following formula (III) or a salt thereof:

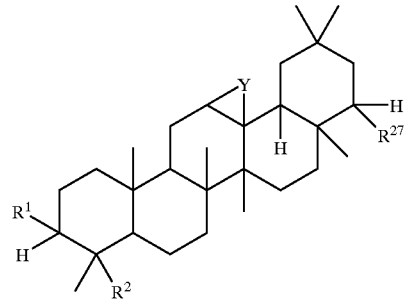

(III)

wherein $R^1$, $R^2$, and Y are as defined above; and $R^{27}$ represents

—O—$(CH_2)_m$—$R^{22}$ wherein $R^{22}$ and m are as defined above,

—$OCOCH(R^{25})(CH_2)_n$—$R^{22}$ wherein $R^{22}$, $R^{25}$, and n are as defined above, —$OCON(R^{29})R^{30}$ wherein $R^{29}$ and $R^{30}$ are as defined above, —$OCO$—$(CH_2)_n$—$R^{16}$ wherein $R^{16}$ is as defined above, or —$OCOCH=CH$—$COOR^6$ wherein $R^6$ is as defined above.

According to the fourth aspect of the present invention, there is provided a pharmaceutical composition for treating a hepatic disorder, comprising as an active ingredient a triterpene derivative represented by the following formula (IV) or a salt thereof:

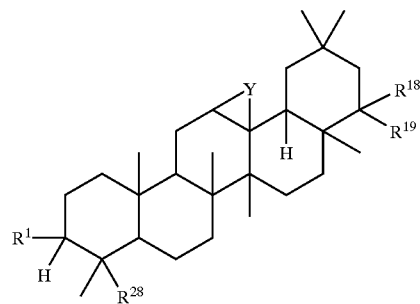

(IV)

wherein $R^1$, $R^{18}$, $R^{19}$, and Y are as defined above; and $R^{28}$ represents —$CON(R^{29})R^{30}$ wherein $R^{29}$ and $R^{30}$ are as defined above, —$C(R^6)_2OH$ wherein $R^6$ is as defined above, —$COR^{6a}$ wherein $R^{6a}$ represents lower alkyl, or —$CH=CHR^6$ wherein $R^6$ is as defined above.

The first group of novel compounds according to the present invention is triterpene derivatives represented by the following formula (Ia) or salts thereof:

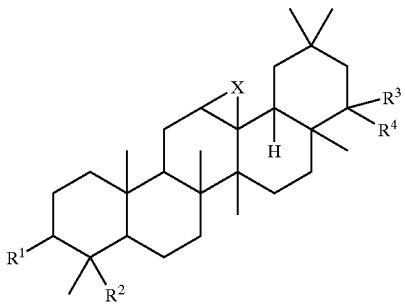

(Ia)

wherein $R^1$ represents a hydroxyl group, lower alkoxy, or lower alkanoyloxy;

$R^2$ represents hydroxymethyl, lower alkoxymethyl, lower alkanoyloxymethyl, or carboxyl;

or $R^1$ and $R^2$ may combine with each other to form —O—C($R^{14}$)$R^{15}$—O—CH$_2$— wherein $R^{14}$ and $R^{15}$, which may be the same or different, represent a hydrogen atom or lower alkyl;

$R^3$ and $R^4$, which may be the same or different, represent a hydrogen atom, a hydroxyl group, lower alkyl, lower alkenyl, aryl, hydroxymethyl, —N($R^{11}$)$R^{12}$ wherein $R^{11}$ and $R^{12}$, which may be the same or different, represent a hydrogen atom, lower alkyl, or lower alkanoyl, formyl, —COOR$^6$ wherein $R^6$ is as defined above, —OR$^{13}$ wherein $R^{13}$ represents lower alkyl, cyclo-lower alkyl, aralkyl, lower alkanoyl, arylcarbonyl, aralkylcarbonyl, lower alkenyl, lower alkenylcarbonyl, or aryl-lower alkenylcarbonyl;

or $R^3$ and $R^4$ may combine with each other to form oxo, hydroxyimino, or alkylidene; and X represents O, CH$_2$, or NH, provided that compounds wherein $R^1$ represents a hydroxyl group, $R^2$ represents hydroxymethyl, $R^3$ represents a hydrogen atom, $R^4$ represents a hydroxyl group and X represents O are excluded.

The second group of novel compounds according to the present invention is triterpene derivatives represented by the following formula (IIa) or salts thereof:

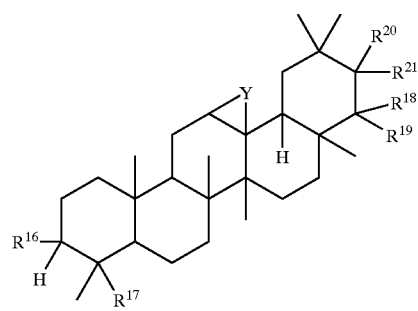

(IIa)

wherein $R^{16}$ represents a hydroxyl group, arylmethyloxy, lower alkoxy, excluding methoxy, or lower alkanoyloxy, excluding acetoxy;

$R^{17}$ represents lower alkyl, lower alkenyl

—CH$_2$OR$^5$ wherein $R^5$ is as defined above, formyl,

—COOR$^6$ wherein $R^6$ is as defined above,

—CH$_2$OCON($R^9$)$R^{10}$ wherein $R^9$ and $R^{10}$ are as defined above,

—CON($R^7$)$R^8$ wherein $R^7$ and $R^8$ are as defined above,

—CH$_2$N($R^7$)$R^8$ wherein $R^7$ and $R^8$ are as defined above,

—C($R^6$)$_2$OH wherein $R^6$ is as defined above,

—COR$^{6a}$ wherein $R^{6a}$ represents lower alkyl, or

—CH=CHR$^6$ wherein $R^6$ is as defined above;

or $R^{16}$ and $R^{17}$ may combine with each other to form —O—C($R^9$)$R^{10}$—O—CH$_2$— wherein $R^9$ and $R^{10}$ are as defined above;

$R^{18}$ and $R^{19}$, which may be the same or different, represent a hydrogen atom, a hydroxyl group, arylmethyloxy, lower alkyl, —N($R^{11}$)$R^{12}$ wherein $R^{11}$ and $R^{12}$ are as defined above, —COOR$^6$ wherein $R^6$ is as defined above, —OR$^{13}$ wherein $R^{13}$ is as defined above, —O—(CH$_2$)$_m$—R$^{22}$ wherein $R^{22}$ represents amino, —NH—COOR$^{23}$ wherein $R^{23}$ represents arylmethyl or lower alkyl, a hydroxyl group, arylmethyloxy, or —COOR$^{24}$ wherein $R^{24}$ represents a hydrogen atom, lower alkyl, or arylmethyl, and m is an integer of 1 to 4, —OCOCH($R^{25}$)(CH$_2$)$_n$—R$^{22}$ wherein $R^{22}$ is as defined above, $R^{25}$ represents a hydrogen atom, lower alkyl, aralkyl, or aryl, and n is an integer of 0 to 3, —OCOCH=CH—COOR$^6$ wherein $R^6$ is as defined above, or —OCON($R^{29}$)$R^{30}$ wherein $R^{29}$ and $R^{30}$ are as defined above;

or $R^{18}$ and $R^{19}$ may combine with each other to form oxo, $R^{20}$ and $R^{21}$ respectively represent the same meanings as $R^{18}$ and $R^{19}$, provided that $R^{20}$ and $R^{21}$ do not represent a hydrogen atom;

or $R^{18}$ and $R^{20}$ may combine with each other to form —O—[C($R^9$)$R^{10}$]$_p$—O— wherein $R^9$ and $R^{10}$ are as defined above and p is an integer of 1 to 3, or —OCO—[C($R^9$)$R^{10}$]$_q$—OCO— wherein $R^9$ and $R^{10}$ are as defined above and q is an integer of 0 to 2; and Y represents O, $CH_2$, NH, or a single bond to form a double bond in the ring with Y bonded thereto;

provided that compounds wherein $R^{16}$ represents a hydroxyl group, $R^{17}$ represents —$CH_2OCH_3$, $R^{20}$ represents a hydroxyl group or methoxy, both $R^{18}$ and $R^{21}$ represent a hydrogen atom, $R^{19}$ represents a hydroxyl group or methoxy and Y represents a single bond, and compounds wherein $R^{16}$ represents a hydroxyl group, $R^{17}$ represents —$CH_2OH$, $R^{20}$ represents a hydroxyl group, $R^{18}$, $R^{19}$, and $R^{21}$ represent a hydrogen atom and Y represents a single bond are excluded.

The third group of novel compounds according to the present invention is compounds represented by the formula (III).

The fourth group of novel compounds according to the present invention is compounds represented by the formula (IV).

BRIEF DESCRIPTION OF THE DRAWING

FIG. 1 is a diagram showing the effect of the pharmaceutical composition for treating a hepatic disorder according to the present invention on hepatitis induced by concanavalin A in mice. Specifically, the alanine aminotransferase (ALT) activity, in plasma, which is an index of hepatopathy was 2068±518 (u/l) for the control group, whereas, for the group of mice which have been treated with the pharmaceutical composition for treating a hepatic disorder according to the present invention, it was lowered to 55±16 (u/l) which was the same level as for the untreated group (that is, normal value).

DETAILED DESCRIPTION OF THE INVENTION

Definition

As used herein, the term "lower alkyl" as a group or a part of a group means both straight and branched lower alkyls which preferably have 1 to 6 carbon atoms, more preferably 1 to 4 carbon atoms. The terms "lower alkenyl" and "lower alkynyl" as a group or a part of a group mean both straight and branched lower alkenyls and lower alkynyls which preferably have 2 to 6 carbon atoms, more preferably 2 to 4 carbon atoms. The term "halogen atom" means a fluorine, chlorine, bromine, or iodine atom. The term "aryl" preferably means phenyl, naphthyl, tolyl, methoxyphenyl or the like. The term "aralkyl" as a group or a part of a group preferably means phenyl $C_{1-4}$ alkyl, more preferably benzyl, phenethyl or the like.

In the compounds of the present invention, examples of the arylmethyloxy include phenylmethyloxy and naphthylmethyloxy.

Examples of the lower alkoxy include straight or branched alkoxys having 1 to 6 carbon atoms, such as methoxy, ethoxy, propoxy, isopropoxy, butoxy, tert-butoxy, pentyloxy, and hexyloxy.

Examples of the lower alkanoyloxy include straight alkanoyloxys having 2 to 6 carbon atoms, such as acetoxy, propionyloxy, butyryloxy, pentanoyloxy, and hexanoyloxy.

Examples of the lower alkanoyl include straight or branched alkanoyls having 1 to 6 carbon atoms, such as formyl, acetyl, propionyl, butyryl, isobutyl, pentanoyl, tert-butylcarbonyl, and hexanoyl.

Examples of the lower alkyl include straight or branched alkyls having 1 to 6 carbon atoms, such as methyl, ethyl, propyl, isopropyl, butyl, tert-butyl, pentyl and hexyl.

Examples of the lower alkenyl include straight or branched alkenyls having 2 to 6 carbon atoms, such as vinyl, allyl, 2-butenyl, 3-butenyl, 1-methylallyl, 2-pentenyl, and 2-hexenyl.

Examples of the aryl include phenyl, naphthyl, and biphenyl.

Examples of the cyclo-lower alkyl include cyclopropyl, cyclopentyl, and cyclohexyl. Examples of the aralkyl include benzyl, phenetyl, and phenylpropyl.

Examples of the arylcarbonyl include benzoyl and naphthylcarbonyl.

Examples of the lower alkenylcarbonyl include straight alkenylcarbonyls having 3 to 6 carbon atoms, such as acryloyl, allylcarbonyl, and 2-butenylcarbonyl.

Examples of the aralkylcarbony include phenylacetyl, phenylpropionyl, and naphthylacetyl. Examples of the aralkenylcarbonyl include cinnamoyl and phenylbutenoyl.

Examples of the alkylidene include ethylidene, propylidene, and butylidene.

For the arylmethyloxy, aryl, aralkyl, arylcarbonyl, aralkylcarbonyl, and aralkenylcarbonyl, at least one hydrogen atom thereon may be substituted with the number of substituents being preferably 1 to 2, and examples of the substituent include methyl, ethyl, methoxy, ethoxy, a halogen atom, amino, dimethylamino, a hydroxyl group, acetoxy, and methylenedioxy.

Pharmaceutical Composition for Treating Hepatic Disorders/Compounds of Formula (I), (II), (III), and (IV)

The compounds represented by the general formula (I), (II), (III), or (IV) and salts thereof are effective for the treatment of hepatic disorders. Hepatic disorders, to which the compounds represented by the general formula (I), (II), (III), or (IV) and salts thereof can be applied, include acute and chronic viral hepatitis, autoimmune hepatitis, and drug-induced, toxic, alcoholic, intrahepatic cholestasis, and inborn metabolic error hepatopathy. The term "hepatopathy" used herein refers to inflammatory hepatic disorders and, depending upon the progress of symptom, is used as a concept embracing also fatty liver, cirrhosis, and hepatoma.

Specifically, the triterpene derivatives represented by the formula (I), (II), (III), or (IV) and salts thereof, when incubated together with human hepatoma cells (Hep G2) in the presence of aflatoxin $B_1$ (hepatopathy-inducing substance), have an inhibitory activity against necrosis of such cells and an inhibitory activity against hepatic disorders in concanavalin A hepatitis virus mice.

The compounds represented by the formula (I), (II), (III), or (IV) have various isomers, and the present invention embraces such isomers and mixtures thereof. Further, the presence of isomers attributable to other group(s) in the formula (I), (II), (III), or (IV) is also considered, and these isomers and mixtures thereof are also embraced in the present invention.

According to a preferred embodiment of the present invention, preferred compounds represented by the formula (I), (II), (III), or (IV) have a configuration represented by the following formula (I-1), (II-1), (III-1), or (IV-1):

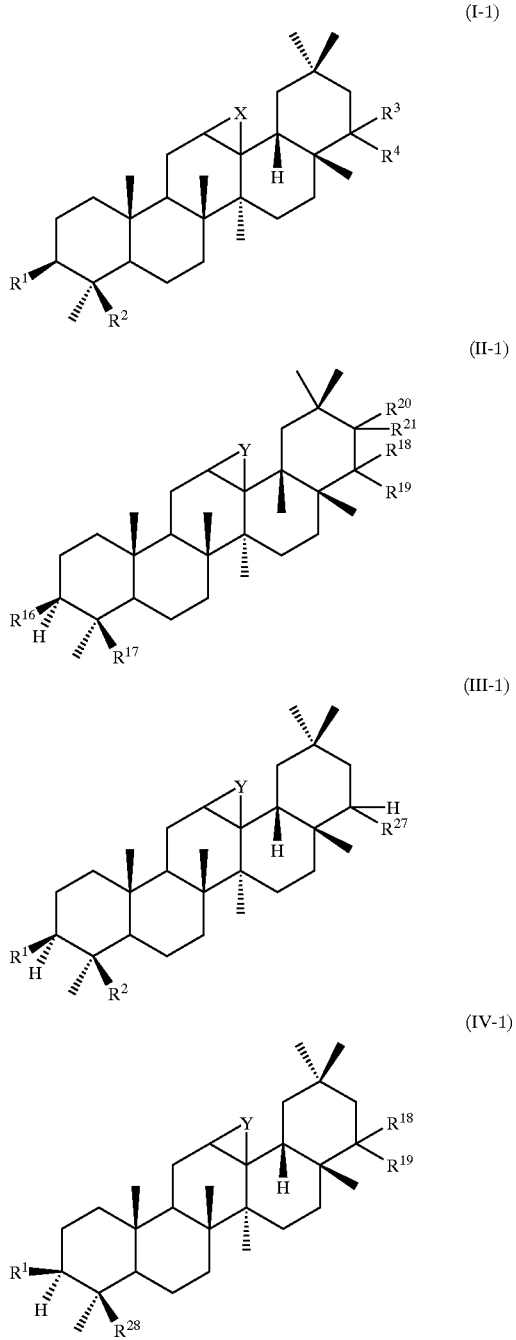

Among the compounds represented by the formula (I), (II), (III), or (IV) according to the present invention, the following groups of compounds are preferred.

For the compounds represented by the formula (I), preferred are:

a group of compounds wherein $R^1$ represents a hydroxyl group, $R^3$ represents a hydrogen atom and X represents O; and a group of compounds wherein $R^1$ represents a hydroxyl group, $R^2$ represents hydroxymethyl, $R^3$ represents a hydrogen atom, $R^4$ represents a hydroxyl group or $-OR^{13}$ and X represents O.

For the compounds represented by the formula (II), preferred are:

a group of compounds wherein $R^{16}$ represents a hydroxyl group, $R^{17}$ represents $-CH_2OH$, both $R^{18}$ and $R^{20}$ represent a hydrogen atom, both $R^{19}$ and $R^{21}$ represent a hydroxyl group and Y represents a single bond to form a double bond in the ring with Y bonded thereto;

a group of compounds wherein $R^{16}$ represents a hydroxyl group, lower alkoxy, or lower alkanoyloxy, $R^{17}$ represents $-CH_2OR^5$, $R^{18}$ represents a hydrogen atom, $R^{19}$ represent $-OR^{13}$, $R^{20}$ represents a hydrogen atom, $R^{21}$ represents $-OR^{13}$ and Y represents a single bond to form a double bond in the ring with Y bonded thereto;

a group of compounds wherein $R^{16}$ represents a hydroxyl group, lower alkoxy, or lower alkanoyloxy, $R^{17}$ represents $-CH_2OR^5$, $R^{18}$ and $R^{19}$ combine with each other to form oxo, $R^{20}$ and $R^{21}$ combine with each other to form oxo and Y represents a single bond to form a double bond in the ring with Y bonded thereto;

a group of compounds wherein $R^{16}$ represents a hydroxyl group, lower alkoxy, or lower alkanoyloxy, $R^{17}$ represents $-CH_2OR^5$, $R^{18}$ and $R^{19}$ combine with each other to form oxo, $R^{20}$ represents a hydrogen atom, $R^{21}$ represents a hydroxyl group and Y represents a single bond to form a double bond in the ring with Y bonded thereto;

a group of compounds wherein $R^{16}$ represents a hydroxyl group, lower alkoxy, or lower alkanoyloxy, $R^{17}$ represents $-CH_2OR^5$, $R^{18}$ and $R^{19}$ represent a hydrogen atom, $R^{20}$ and $R^{21}$ combine with each other to form oxo and Y represents a single bond to form a double bond in the ring with Y bonded thereto;

a group of compounds wherein $R^{16}$ represents a hydroxyl group, lower alkoxy, excluding methoxy, or lower alkanoyloxy, excluding acetoxy, $R^{17}$ represents $-CH_2OR^5$, $R^{18}$ and $R^{19}$ represent a hydrogen atom, $R^{20}$ represents a hydrogen atom, $R^{21}$ represents a hydroxyl group and Y represents a single bond to form a double bond in the ring with Y bonded thereto;

a group of compounds wherein $R^{16}$ represents a hydroxyl group, $R^{17}$ represents $-CH_2OR^5$, $R^{18}$ represents a hydrogen atom, $R^{19}$ represents a hydroxyl group or $-OR^{13}$, $R^{20}$ represents a hydrogen atom, $R^{21}$ represents a hydroxyl group or $-OR^{13}$ and Y represents a single bond and, thus, represents O;

a group of compounds wherein $R^{16}$ represents a hydroxyl group, lower alkoxy, or lower alkanoyloxy, $R^{17}$ represents $-C(R^6)_2OH$, $R^{18}$ represents a hydrogen atom, $R^{19}$ represents a hydroxyl group or $-OR^{13}$, $R^{20}$ represents a hydrogen atom, $R^{21}$ represents a hydroxyl group or $-OR^{13}$ and Y represents a single bond to form a double bond in the ring with Y bonded thereto;

a group of compounds wherein $R^{16}$ represents a hydroxyl group, lower alkoxy, or lower alkanoyloxy, $R^{17}$ represents $-COR^{6a}$, $R^{18}$ represents a hydrogen atom, $R^{19}$ represents a hydroxyl group or $-OR^{13}$, $R^{20}$ represents a hydrogen atom, $R^{21}$ represents a hydroxyl group or $-OR^{13}$ and Y represents a single bond to form a double bond in the ring with Y bonded thereto; and a group of compounds wherein $R^{16}$ represents a hydroxyl group, lower alkoxy, or lower alkanoyloxy, $R^{17}$ represents $-CH=CHR^6$, $R^{18}$ represents a hydrogen atom, $R^{19}$ represents a hydroxyl group or $-OR^{13}$, $R^{20}$ represents a hydrogen atom, $R^{21}$ represents a hydroxyl group or $—OR^{13}$ and Y represents a single bond to form a double bond in the ring with Y bonded thereto.

For the compounds represented by the formula (III), preferred are:

a group of compounds wherein $R^1$ represents a hydroxyl group, lower alkoxy, or lower alkanoyloxy, $R^2$ represents $—CH_2OR^5$, $R^{27}$ represents $—OCO—(CH_2)_n—R^{16}$ and Y represents a single bond to form a double bond in the ring with Y bonded thereto;

a group of compounds wherein $R^1$ represents a hydroxyl group, lower alkoxy, or lower alkanoyloxy, $R^2$ represents $—CH_2OR^5$, $R^{27}$ represents $—O—(CH_2)_m—R^{22}$ and Y represents a single bond to form a double bond in the ring with Y bonded thereto;

a group of compounds wherein $R^1$ represents a hydroxyl group, lower alkoxy, or lower alkanoyloxy, $R^2$ represents $—CH_2OR^5$, $R^{27}$ represents $—OCOCH(R)(CH_2)_n—R^{22}$ or $—OCOCH=CH—COOR^6$ and Y represents a single bond to form a double bond in the ring with Y bonded thereto; and a group of compounds wherein $R^1$ represents a hydroxyl group, lower alkoxy, or lower alkanoyloxy, $R^2$ represents $—CH_2OR^5$, $R^{27}$ represents $—OCON(R^{29})R^{30}$ and Y represents a single bond to form a double bond in the ring with Y bonded thereto.

For the compounds represented by the formula (IV), preferred are:

a group of compounds wherein $R^{18}$ and $R^{19}$ represent a hydrogen atom, a hydroxyl group, or $—OR^{13}$, $R^{28}$ represents $—CON(R^{29})R^{30}$ wherein $R^{29}$ and $R^{30}$ are as defined above, $—C(R^6)_2OH$ wherein $R^6$ is as defined above, $—COR^{6a}$ wherein $R^{6a}$ is as defined above, or $—CH=CHR^6$ wherein $R^6$ is as defined above.

The compounds represented by the formula (I), (II), (III), or (IV) according to the present invention may be present in the form of a salt. The salt may be formed by simply reacting the above compounds with a pharmaceutically acceptable base according to a conventional method. In this case, inorganic bases, such as sodium hydroxide, potassium hydroxide, aluminum hydroxide, sodium carbonate, potassium carbonate, and sodium hydrogencarbonate, and organic bases, such as piperazine, morpholine, piperidine, ethylamine, and trimethylamine, may be used as the base.

Although the compound according to the present invention may be administered as a raw material, it may be preferably administered as a pharmaceutical composition. Pharmaceutical compositions, as pharmaceutical compositions for hepatic disorders, comprising as an active ingredient the compound or salts thereof according to the present invention can be administered either orally or parenterally (e.g., intravenous injection, intramuscular injection, subcutaneous administration, rectal administration, or percutaneous administration) to humans or animals other than humans.

Therefore, the pharmaceutical compositions for hepatic disorders according to the present invention may be made into a preparation suitable for the route of administration. Specifically, it may be mainly made into any of the following preparations: an injection such as intravenous or intramuscular injection; an oral preparation such as a capsule, a tablet, a granule, a powder, a pill, fine subtilaes, or a troche; a preparation for rectal administration; an oleaginous suppository; and an aqueous suppository. The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include milk sugar, fruit sugar, grape sugar, starch, gelatin, magnesium carbonate, synthetic magnesium silicate, talc, magnesium stearate, methyl cellulose, carboxymethyl cellulose or a salt thereof, gum arabic, polyethylene glycol, syrup, vaseline, glycerin, ethanol, propylene glycol, citric acid, sodium chloride, sodium sulfite and sodium phosphate.

The dosage of the compound represented by the formula (I) may vary depending upon the age, weight, conditions, or severity of the disease of a patient. In general, however, it is approximately 0.1 to 1000 mg, preferably 1 to 100 mg per day for adult human, once or twice a day. The administration may be made either orally or parenterally.

Group of Novel Compounds/Compounds of Formula (Ia), (IIa), (III), and (IV)

According to another aspect of the present invention, there are provided novel triterpene derivatives represented by the formula (Ia), (IIa), (III), or (IV).

Preferred examples of each group in these formulae may be the same as those described above in connection with the formulae (I), (II), (III), and (IV).

In the above definition of the formula (IIa), for $R^{16}$, methoxy was excluded from the lower alkoxy and acetoxy was excluded from the lower alkanoyloxy. Regarding the following groups of compounds, however, methoxy is embraced in the lower alkoxy represented by $R^{16}$ and acetoxy is embraced in the lower alkanoyloxy represented by $R^{16}$. Specifically, such groups of compounds are:

a group of compounds wherein $R^{16}$ represents a hydroxyl group, lower alkoxy, or lower alkanoyloxy, $R^{17}$ represents $—CH_2OR^5$, $R^{18}$ represents a hydrogen atom, $R^{19}$ represents $—OR^{13}$, $R^{20}$ represents a hydrogen atom, $R^{21}$ represents $—OR^{13}$ and Y represents a single bond to form a double bond in the ring with Y bonded thereto;

a group of compounds wherein $R^{16}$ represents a hydroxyl group, lower alkoxy, or lower alkanoyloxy, $R^{17}$ represents $—CH_2OR^5$, $R^{18}$ and $R^{19}$ combine with each other to form oxo, $R^{20}$ and $R^{21}$ combine with each other to form oxo and Y represents a single bond to form a double bond in the ring with Y bonded thereto;

a group of compounds wherein $R^{16}$ represents a hydroxyl group, lower alkoxy, or lower alkanoyloxy, $R^{17}$ represents $—CH_2OR^5$, $R^{18}$ and $R^{19}$ combine with each other to form oxo, $R^{20}$ represents a hydrogen atom, $R^{21}$ represents a hydroxyl group and Y represents a single bond to form a double bond in the ring with Y bonded thereto; and a group of compounds wherein $R^{16}$ represents a hydroxyl group, lower alkoxy, or lower alkanoyloxy, $R^{17}$ represents $—CH_2OR^5$, $R^{18}$ and $R^{19}$ represents a hydrogen atom, $R^{20}$ and $R^{21}$ combine with each other to form oxo and Y represents a single bond to form a double bond in the ring with Y bonded thereto.

For these novel compounds, preferred groups of compounds represented by the formulae (I), (II), (III), and (IV) and preferred configuration thereof may be the same as described above in connection with the above formulae (I), (II), (III), and (IV).

The compounds represented by the formulae (Ia), (IIa), (III), or (IV) also have various isomers, and the present invention embraces all of such isomers and mixtures thereof. Further, the presence of isomers attributable to other group(s) in the formula (Ia), (IIa), (III), or (IV) is also considered, and these isomers and mixtures thereof are also embraced in the present invention. The compounds represented by the formulae (Ia), (IIa), (III), or (IV) also may be easily converted to the corresponding salts by allowing a pharmaceutically acceptable base to act on the compounds. Preferred bases may be the same as those described above in connection with the formulae (I), (II), (III), and (IV).

Preparation of Compounds

Process (A)

Among the compounds represented by the formula (I), the compound represented by the formula (VI), wherein $R^1$, $R^2$, $R^3$ and $R^4$ are as defined above, may be prepared by reacting a compound represented by the following formula (V), wherein $R^1$, $R^2$, $R^3$ and $R^4$ are as defined above, with a suitable oxidizing agent.

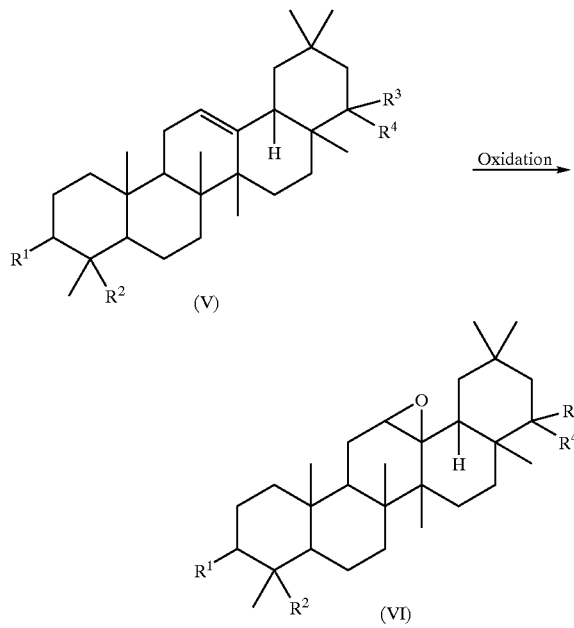

Solvents usable in this reaction include, for example, dichloromethane, chloroform, benzene, and toluene. Oxidizing agents usable herein include, for example, perbenzoic acid, m-chloroperbenzoic acid, and peracetic acid. In general, the oxidizing agent is used in an amount of 1 to 3 equivalents based on the compound represented by the formula (V). The reaction may be usually carried out at 0 to 60° C.

Process (B)

Among the triterpene derivatives represented by the formula (I), the compound represented by the following formula (VII), wherein $R^1$, $R^2$, $R^3$ and $R^4$ are as defined above, may be prepared by reacting a compound represented by the following formula (V) with a cyclopropanating agent.

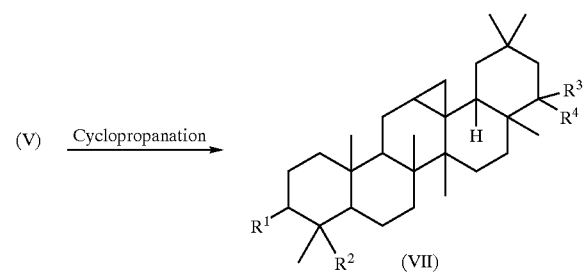

Solvents usable herein include benzene, toluene, hexane, diethyl ether, tetrahydrofuran, and 1,2-dichloroethane. Cyclopropanating agents usable herein include Zn(Cu)—$CH_2I_2$ and $Et_2Zn$—$CH_2I_2$. In general, the cyclopropanating agent is used in an amount of 1 to 10 equivalents based on the compound represented by the formula (V). The reaction may be usually carried out at —40 to 60° C. The addition of a Lewis acid, such as titanium tetrachloride, to this reaction system often accelerates the reaction.

Process (C)

Among the compounds represented by the formula (I), the compound represented by the formula (VIII), wherein $R^1$, $R^2$, $R^3$ and $R^4$ are as defined above, may be prepared by reacting the compound represented by the formula (V) with $IN_3$ and subsequently with a suitable reducing agent.

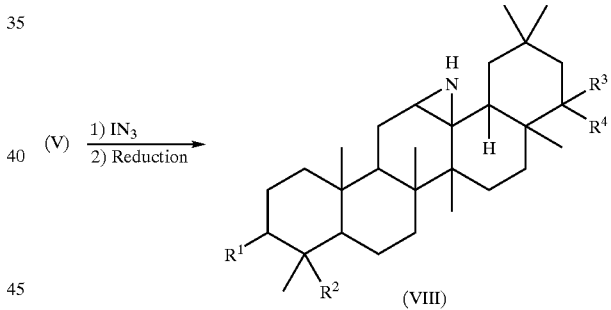

In general, $IN_3$ is used in an amount of 1 to 3 equivalents based on the compound represented by the formula (V). Solvents usable in this reaction include DMF and acetonitrile. The reaction may be carried out at 0 to 40° C. Lithium aluminum hydride may be used as the reducing agent in an amount of 1 to 5 equivalents, and solvents usable in this reaction with the reducing agents include diethyl ether and tetrahydrofuran. The reaction with the reducing agent may be carried out at 0 to 60° C.

Process (D)

Among the compounds represented by the formula (II), the compound represented by the formula (X), wherein $R^{18}$, $R^{19}$, $R^{20}$ and $R^{21}$ are as defined above, may be prepared by reacting a compound represented by the following formula (IX), wherein $R^{18}$, $R^{19}$, $R^{20}$ and $R^{21}$ are as defined above, with a suitable oxidizing agent.

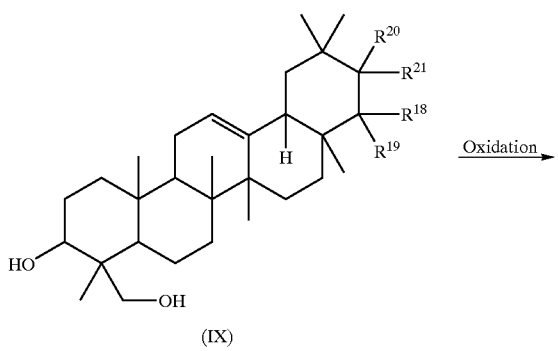

(IX)

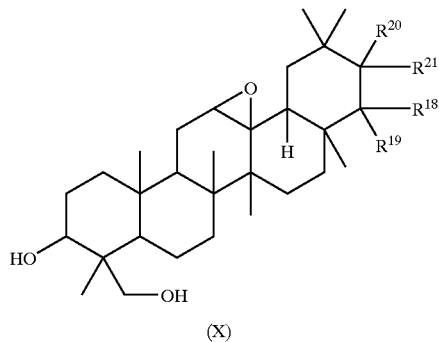

(X)

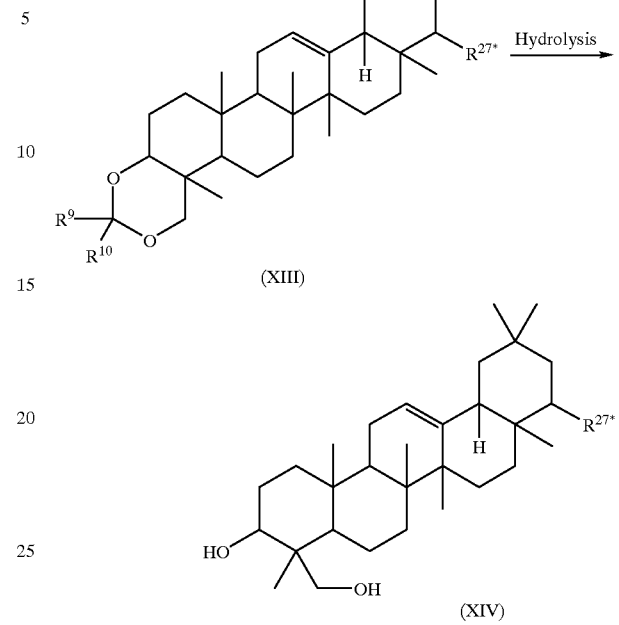

(XIII)

(XIV)

Solvents usable in this reaction include, for example, dichloromethane, chloroform, benzene, and toluene. Oxidizing agents usable herein include, for example, perbenzoic acid, m-chloroperbenzoic acid, and peracetic acid. In general, the oxidizing agent is used in an amount of 1 to 3 equivalents based on the compound represented by the formula (V). The reaction may be usually carried out at 0 to 60° C.

Process (E)

Among the compounds represented by the formula (III), the compound represented by the formula (XIV), wherein $R^{27*}$ represents —O—$(CH_2)_m$—$R^{22}$, —OCOCH($R^{25}$)$(CH_2)_n$—$R^{22}$, —OCON($R^{29}$)$R^{30}$, —OCO—$(CH_2)_n$—$R^{16}$, or —OCOCH=CH—COOR$^6$, and $R^{16}$, $R^{22}$, $R^{25}$, $R^{29}$, $R^{30}$, n and m are as defined above, can be prepared by the following reaction.

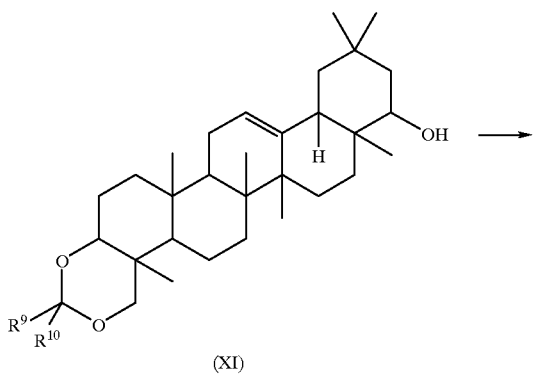

(XI)

At the outset, a compound represented by the formula (XI), wherein $R^9$ and $R^{10}$ are as defined above, is reacted with a compound represented by the formula —Z—$(CH_2)_m$—$R^{22}$, wherein Z represents a halogen atom, Cl—COCH($R^{25}$) $(CH_2)_n$—$R^{22}$, $R^{29}$—NCO, Cl—CO—$(CH_2)_n$—$R^6$, or Cl—COCH=CH—COOR$^6$ in the presence or absence of a base to give a compound represented by the formula (XIII) wherein $R^9$, $R^{10}$, $R^{10}$, $R^{27*}$ and m are as defined above. Solvents usable herein include diethyl ether, tetrahydrofuran, benzene, toluene, dichloromethane, chloroform, or dimethylformamide. Bases usable herein include, for example, triethylamine, pyridine, 4-dimethylaminopyridine, sodium hydride, potassium hydride, n-butyllithium, NaCH$_2$SOCH$_3$, and tert-BuOK. The compound represented by the formula —Z—$(CH_2)_m$— $R^{22}$, wherein Z represents a halogen atom, Cl—COCH($R^{25}$) $(CH_2)_n$—$R^{22}$, $R^{29}$—NCO, Cl—CO—$(CH_2)_n$—$R^{16}$, or Cl—COCH=CH—COOR$^6$ may be used in an amount of 1 to 3 equivalents based on the compound represented by the formula (XI).

The base may be usually used in an amount of 1 to 10 equivalents based on the compound represented by the formula (XI) and, in some cases, may be used as a solvent. The reaction may be carried out at −60 to 60° C. The base may be usually used in an amount of 1 to 10 equivalents based on the compound represented by the formula (XI) and, in some cases, may be used as a solvent. The reaction may be carried out at −20 to 60° C.

The compound represented by the formula (XIII) may be hydrolyzed in the presence of an acid to prepare the compound represented by the formula (XIV). Solvents usable herein include methanol, ethanol, propanol, water, dichloromethane, and chloroform. Acids usable herein include mineral acids, such as hydrochloric acid and sulfuric acid, and Lewis acids, such as BF$_3$.Et$_2$O. In general, the reaction may be carried out at 0 to 120° C.

Process (F)

Among the compounds represented by the formula (IV), the compound represented by the formula (XVIII) can be prepared by the following process.

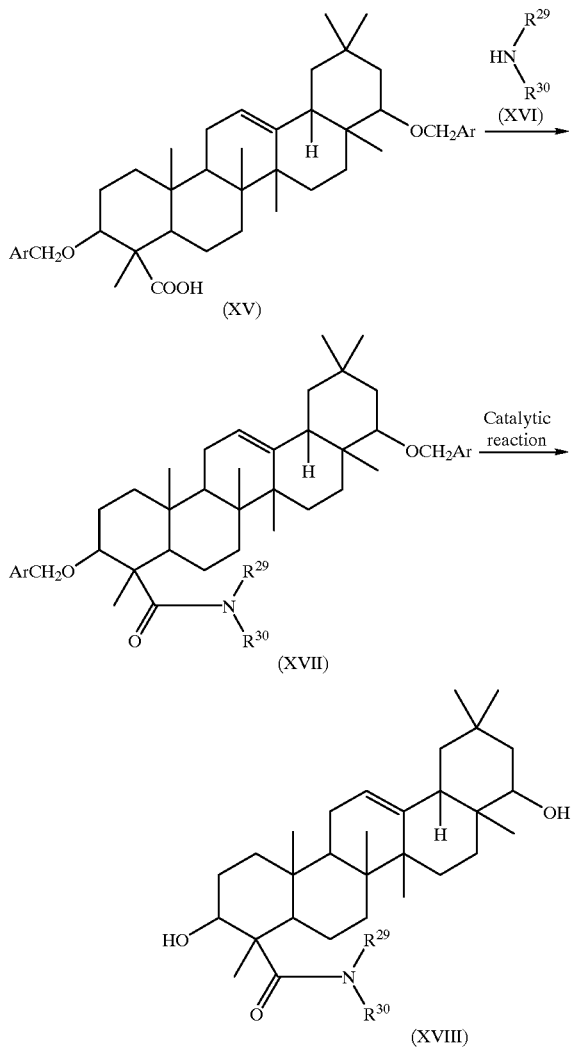

At the outset, a compound represented by the formula (XV), wherein Ar represents aryl, is reacted with a compound represented by the formula (XVI), wherein $R^{29}$ and $R^{30}$ are as defined above, in the presence of a suitable condensing agent to give a compound represented by the formula (XVII), wherein Ar, $R^{29}$ and $R^{30}$ are as defined above. Solvents usable herein include, for example, dichloromethane, chloroform, benzene, toluene, tetrahydrofuran, and diemthylformamide. Condensing agents usable herein include dicyclohexylcarbodiimide (DCC), DCC-hydroxybenzotriazole, benzotriazol-1-yl-oxytris(dimethylamino)phosphonium hexafluorophosphate (BOP reagent), and diphenylphosphorylazide. The condensing agent may be used in an amount of 1 to 3 equivalents based on the compound represented by the formula (XV). In general, the reaction may be carried out at −20 to 60° C.

The compound represented by the formula (XVII) may be catalytically reduced in the presence of a catalyst to prepare the compound represented by the formula (XVIII). Solvent usable herein include, for example, water, methanol, ethanol, tetrahydrofuran, dioxane, dichloromethane, and chloroform. Catalysts usable herein include, for example, Pd—C, Pd-black, and Pd(OH)$_2$—C. The catalyst may be used in an amount of 0.1 to 0.6 equivalent based on the compound represented by the formula (XVII). In general, the reaction may be carried out at room temperature in a hydrogen atmosphere of 1 to 4 atm.

The hydroxyl group of the compound represented by the formula (XVII) may be further modified to give the compound represented by the formula (IV).

The compound represented by the formula (XV) may be prepared by the following process.

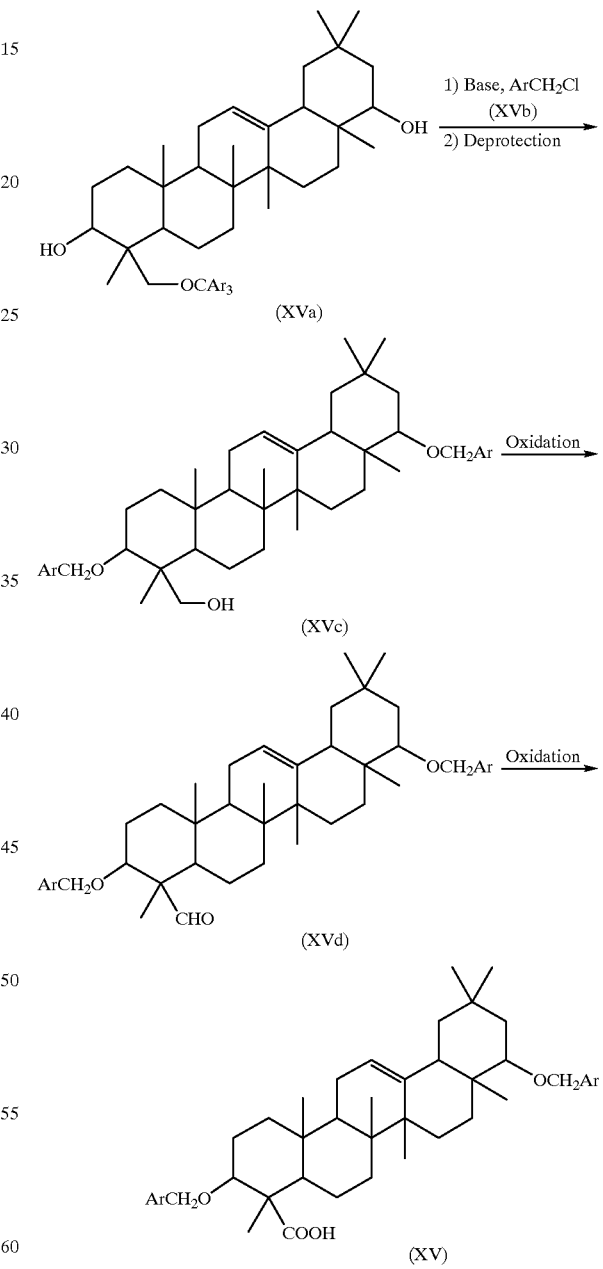

A compound represented by the formula (XVa) may be reacted with a compound represented by the formula (XVb) in the presence of a base, followed by deprotection of the triaryl group to give a compound represented by the formula (XVc) wherein Ar represents aryl group. Solvents usable herein include diethyl ether, THF, DMF, dimethylsulfoxide (DMSO), benzene, and toluene. Bases usable herein include, for example, sodium hydride, potassium hydride, n-butyllithium, $NaCH_2SOCH_3$, and tert-BuOK. Preferably, the base and the compound represented by the formula (XVb) are used in an amount of 1 to 10 equivalents based on the compound represented by the formula (XVa). Preferably, the reaction is carried out at −78 to 60° C. The deprotection may be carried out in the presence of a mineral acid, such as hydrochloric acid or sulfuric acid, in a solvent, such as methanol, ethanol, isopropyl alcohol (IPA), or water, at a temperature of 0 to 80° C.

The compound represented by the formula (XVc) may be then oxidized with a suitable oxidizing agent to give a compound represented by the formula (XVd). Oxidizing agents usable herein include, for example, pyridinium chromate, pyridinium dichromate, manganese dioxide, and DMSO oxidizing reagents, such as DMSO-oxalyl chloride. Solvents usable in this reaction include dichloromethane, chloroform, diethyl ether, and THF. Preferably, the oxidizing agent is used in an amount of 1 to 5 equivalents based on the compound represented by the formula (XVc). The reaction may be usually carried out at −78 to 40° C.

The compound represented by the formula (XVd) may be further oxidized with a suitable oxidizing agent to prepare the compound represented by the formula (XV). Solvents usable herein include, for example, DMF, tert-butanol, acetone, and water. Oxidizing agents usable herein include, pyridinium dichromate, Jones reagent, potassium permanganate, and sodium chlorite. The oxidizing agent may be used in an amount of 1 to 30 equivalents based on the compound represented by the formula (XVd). The reaction may be carried out at 0 to 60° C.

Process (G)

The compound represented by the formula (I), wherein $R^1$ represents lower alkoxy or lower alkanoyloxy and $R^2$ represents —$CH_2OR^5$ (wherein $R^5$ represents lower alkyl or lower alkanoyl), the compound represented by the formula II, wherein $R^{16}$ represents arylmethyloxy, lower alkoxy, or lower alkanoyloxy and $R^{17}$ represents —$CH_2OR^5$ (wherein $R^5$ represents lower alkyl or lower alkanoyl), and the compound represented by the formula (III), wherein $R^1$ represents lower alkoxy or lower alkanoyloxy, and $R^2$ represents —$CH_2OR^5$ (wherein $R^5$ represents lower alkyl or lower alkanoyl, may be prepared by reacting respectively the compound represented by the formula (I), wherein $R^1$ represents a hydroxyl group and $R^2$ represents —$CH_2OH$, the compound represented by the formula (II), wherein $R^{16}$ represents a hydroxyl group and $R^{17}$ represents —$CH_2OH$, and the compound represented by the formula (III), wherein $R^1$ represents a hydroxyl group and $R^2$ represents —$CH_2OH$, with a compound represented by the formula $R^5Z$ or $(R^{5a})_2O$, wherein $R^{5a}$ represents lower alkyl or lower alkanoyl, in the presence of a base. Solvents usable in this reaction include diethyl ether, tetrahydrofuran, benzene, toluene, dichloromethane, chloroform, and dimethylformamide. Bases usable herein include, for example, triethylamine, pyridine, and 4-dimethylaminopyridine. Preferably, the compound represented by the formula $R^5Z$ or $(R^{5a})_2O$ is used in an amount of 1 to 3 equivalents based on the compounds represented by the formulae (I), (II), and (III). The base is used in an amount of preferably 1 to 10 equivalents based on the compounds represented by the formulae (I), (II), and (III) and, in some cases, may be used as a solvent. The reaction may be carried out at −20 to 60° C.

Process (H)

Among the compounds represented by the formula (II), the compound represented by the formula (XIX), wherein $R^*$ represents —$OR^{13}$, O—$(CH_2)_m$—$R^{22}$, —$OCOCH(R^{25})$ $(CH_2)_n$—$R^{22}$, —$OCOCH=CH$—$COOR^6$, or —$OCON$ $(R^{29})R^{30}$, may be prepared by the following reaction.

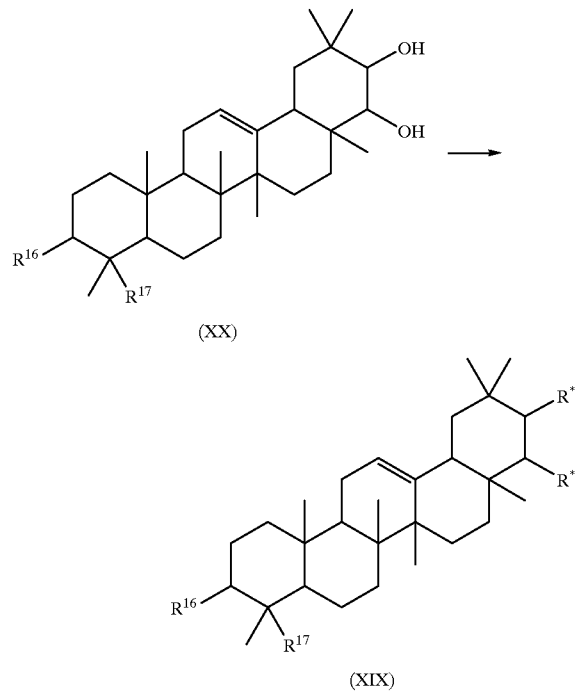

At the outset, a compound represented by the formula (XX) may be reacted with a compound represented by the formula $R^{13}Z$, wherein Z represents a halogen atom, $(R^{13})_2$ O, Cl—$COCH(R^{25})(CH_2)_n$—$R^{22}$, Cl—$COCH=CH$— $COOR^6$, or $R^{29}$—NCO, in the presence of a base to give the compound represented by the formula (XIX). Solvents usable in this reaction include, for example, diethyl ether, tetrahydrofuran, benzene, toluene, dichloromethane, chloroform, and dimethylformamide. Bases usable herein include, for example, triethylamine, pyridine, and 4-dimethylaminopyridine. The compound represented by the formula $R^{13}Z$, wherein Z represents a halogen atom, $(R^{13})_2O$, Cl—$COCH(R^{25})(CH_2)_n$—$R^{22}$, $R^{29}$—NCO, Cl—CO—$(CH_2)_n$—$R^{16}$, or Cl—$COCH=CH$—$COOR^6$ is used in an amount of 1 to 3 equivalents based on the compound represented by the formula (XX). In general, the base is used in an amount of 1 to 10 equivalents based on the compound represented by the formula (XX) and, in some cases, used as a solvent. The reaction may be carried out at −60 to 60° C.

Among the compounds represented by the formula (II), the compound represented by the formula (XIX), wherein $R^*$ represents —$OR^{13}$ or —$O$—$(CH_2)_m$—$R^{22}$, may be prepared by reacting a compound represented by the formula (II), wherein $R^{18}$ represents a hydrogen atom, $R^{19}$ represents a hydroxyl group, $R^{20}$ represents a hydrogen atom and $R^{21}$ represents a hydroxyl group, with a compound represented by the formula $R^{13}Z$ or $Z$—$(CH_2)_m$—$R^{22}$, wherein Z represents a halogen atom, in the presence of a base. Solvents usable herein include, for example, diethyl ether, THF, benzene, toluene, DMF, and DMSO. Bases usable herein include, for example, sodium hydride, potassium hydride, n-butyllithium, NaCH$_2$SOCH$_3$, and tert-BuOK. Preferably, the base and the compound represented by R$^{13}$Z or Z—(CH$_2$)$_m$—R$^{22}$ are used in an amount of 1 to 10 equivalents based on the compound represented by the formula (II). Preferably, the reaction is carried out at −78 to 60° C.

Process (I)

The compound represented by the formula (I), wherein R$^3$ and R$^4$ combine with each other to form oxo, the compound represented by the formula (II), wherein R$^{18}$ and R$^{19}$ combine with each other to form oxo, and/or R$^{20}$ and R$^{21}$ combine with each other to form oxo, and the compound represented by the formula (IV), wherein R$^{18}$ and R$^{19}$ combine with each other to form oxo, may be prepared respectively by oxidizing the compound represented by the formula (I), wherein R$^3$ represents a hydrogen atom and R$^4$ represents a hydroxyl group, the compound represented by the formula (II), wherein R$^{18}$ and R$^{20}$ represent a hydrogen atom and both R$^{19}$ and R$^{21}$ represent a hydroxyl group or alternatively any one of R$^{19}$ and R$^{21}$ represents a hydroxyl group with the other substituent representing a hydrogen atom, and the compound represented by the formula (IV), wherein R$^{18}$ represent a hydrogen atom and R$^{19}$ represents a hydroxyl group, with an oxidizing agent. Oxidizing agents usable herein include, for example, pyridinium chromate, pyridinium dichromate, manganese dioxide, and DMSO oxidizing reagents, such as DMSO-oxalyl chloride. Solvents usable in this reaction include dichloromethane, chloroform, diethyl ether, and THF. Preferably, the oxidizing agent is used in an amount of 1 to 5 equivalents. The reaction may be usually carried out at −78 to 40° C.

Process (J)

The compound represented by the formula (I), wherein R$^3$ represents a hydrogen atom and R$^4$ represents a hydroxyl group, the compound represented by the formula (II), wherein R$^{18}$ and R$^{20}$ represent a hydrogen atom and both R$^{19}$ and R$^{21}$ represents a hydroxyl group or alternatively any one of R$^{19}$ and R$^{21}$ represent a hydroxyl group with the other substituent representing a hydrogen atom, and the compound represented by the formula (IV), wherein R$^{18}$ represents a hydrogen atom and R$^{19}$ represents a hydroxyl group, may be prepared respectively by reducing the compound represented by the formula (I), wherein R$^3$ and R$^4$ combine with each other to form oxo, the compound represented by the formula (II), wherein R$^{18}$ and R$^{19}$ combine with each other to form oxo, and/or R$^{20}$ and R$^{21}$ combine with each other to form oxo, and the compound represented by the formula (IV), wherein R$^{18}$ and R$^{19}$ combine with each other to form oxo, with a reducing agent. Reducing agents usable herein include, for example, lithium aluminum hydride and sodium boron hydride. In general, the reducing agent may be used in an amount of 1 to 5 equivalents. Solvents usable herein include, for example, diethyl ether, THF, benzene, toluene, and dichloromethane. The reaction may be carried out at −78 to 60° C.

Process (K)

Among the compounds represented by the formula (II), the compound represented by the formula (XXI) may be prepared by the following process.

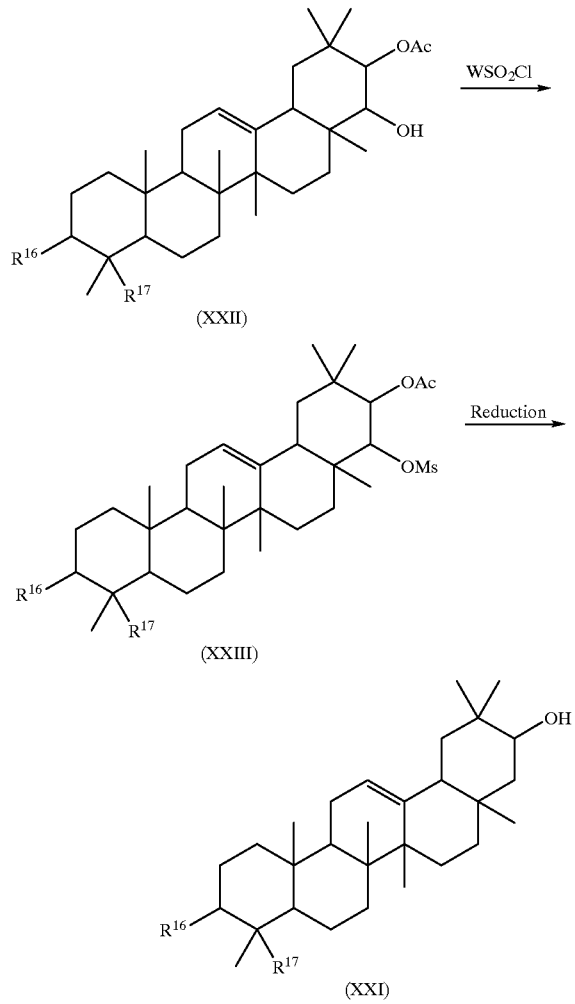

At the outset, a compound represented by the formula (XXII) may be reacted with a compound represented by the formula WSO$_2$Cl, wherein W represents alkyl or aryl, in the presence of a base to give the compound represented by the formula (XXIII). Solvents usable herein include benzene, toluene, dichloromethane, chloroform, diethyl ether, THF, and DMF. Specific examples of compounds represented by the formula WSO$_2$Cl include, for example, methanesulfonyl chloride, benzenesulfonyl chloride, and p-toluenesulfonyl chloride. Bases usable herein include, for example, triethylamine, pyridine, and 4-dimethylaminopyridine. In general, the compound represented by the formula WSO$_2$Cl and the base are used in an amount of 1 to 3 equivalents based on the compound represented by the formula (XXII). The reaction may be usually carried out at 0 to 60° C.

The compound represented by the formula (XXIII) may be reacted with a reducing agent to give the compound represented by the formula (XXI). Solvents usable in this reaction include, for example, diethyl ether, THF, benzene, toluene, and dichloromethane. Reducing agents usable herein include, for example, triethylboronlithium hydride, and may be usually used in an amount of 1 to 5 equivalents. The reaction may be carried out at a temperature of −78 to 60° C.

Process (L)

The compound represented by the formula (IV), wherein R$^{28}$ represents —C(R$^6$)$_2$OH, may be prepared by reacting a compound represented by the formula (IV), wherein $R^{28}$ represents —CHO, with a compound represented by the formula $(R^6)_iMZ_j$, wherein $R^6$ is as defined above, M represents lithium, magnesium, zinc, or aluminum, Z represents a halogen atom, i is an integer of 1 to 3, and j is 0 or 1. Solvents usable in this reaction include diethyl ether, THF, benzene, toluene, hexane, dimethylformamide (DMF), hexamethylphosphorustriamide, and dichloromethane. Preferably, the compound represented by the formula $(R^6)_iMZ_j$ is used in an amount of 1 to 3 equivalents based on the compound represented by the formula (IV). In general, the reaction may be carried out at −78 to 20° C.

Process (M)

The compound represented by the formula (IV), wherein $R^{28}$ represents —CH=CHR$^6$, may be prepared by reacting the compound represented by the formula (IV), wherein $R^{28}$ represents —CHO, with an olefinating reagent. Solvents usable herein include dichloromethane, chloroform, diethyl ether, THF, DMF, and DMSO. Olefinating reagents usable herein include, for example, $Ph_3P$=$CHR_6$, Tebbe reagent, and Nysted reagent. Preferably, the olefinating reagent is used in an amount of 1 to 10 equivalents based on the compound represented by the formula (IV). In general, the reaction may be carried out at −78 to 40° C. The addition of a Lewis acid, such as titanium tetrachloride, to this reaction system often accelerates the reaction and, hence, is preferred.

Process (N)

The compound represented by the formula (IV), wherein $R^{28}$ represents —COR$^6$ or —C(R$^6$)OH, may be prepared by reacting the compound represented by the formula (II), wherein $R^{28}$ represents —COOR$^6$, with a compound represented by the formula $(R^6)_iMZ_j$, wherein $R^6$ is as defined above, M represents lithium, magnesium, zinc, or aluminum, Z represents a halogen atom, i is an integer of 1 to 3, and j is 0 or 1. Solvents usable in this reaction include diethyl ether, THF, benzene, toluene, hexane, dimethylformamide (DMF), hexamethylphosphorustriamide, and dichloromethane. Preferably, the compound represented by the formula $(R^6)_iMZ_j$ is used in an amount of 1 to 3 equivalents based on the compound represented by the formula (IV). In general, the reaction may be carried out at −78 to 20° C.

It would be apparent to a person having ordinary skill in the art that various compounds embraced in the compounds represented by the formulae (I), (II), (III), and (IV) may be prepared by using the above processes (A) to (M) in combination. Further, in the above methods, previously protecting a functional group, which is not involved in the reaction or is unfavorable to be involved in the reaction, is apparent to a person having ordinary skill in the art. In this connection, utilization of protective groups commonly used in the art are also apparent to a person having ordinary skill in the art.

EXAMPLES

The present invention will be described in more detail with reference to the following examples, though it is not limited to these examples only.

Structures of the following compounds 1 to 74 are summarized in the following table. In the following table, the formula (A) is a structural formula formed by collectively generalizing the structures respectively represented by the formulae (I), (II), (III), and (VI).

Compounds 3, 11, 18, and 21 were produced according to a process described in Chem. Pharm. Bull., 36, 153 (1988), and compounds 1 and 7 were produced according to processes described in Ber., 70, 2083, 2093 (1937), Ber., 71, 790, 1604 (1938), Chem. Pharm. Bull., 31, 664 (1983), and Chem. Pharm. Bull., 31, 674 (1983).

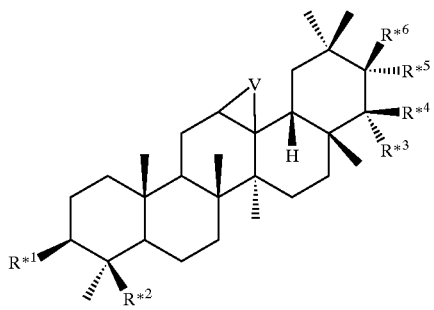

(A)

| compound | $R^{*1}$ | $R^{*2}$ | $R^{*3}$ | $R^{*4}$ | $R^{*5}$ | $R^{*6}$ | V |
|---|---|---|---|---|---|---|---|
| 1 | OH | CH$_2$OH | H | OH | H | H | = |
| 2 | OH | CH$_2$OH | H | OH | H | H | O |
| 3 |  | OCMe$_2$OCH$_2$ | H | OH | H | H | = |
| 4 |  | OCMe$_2$OCH$_2$ | H | OMe | H | H | = |
| 5 | OH | CH$_2$OH | H | OMe | H | H | = |

-continued

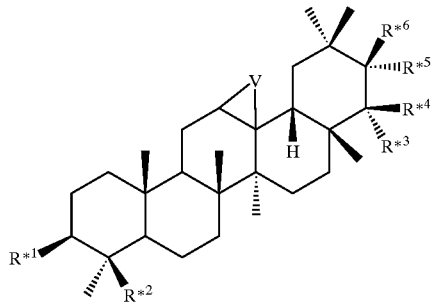

(A)

| compound | R*1 | R*2 | R*3 | R*4 | R*5 | R*6 | V |
|---|---|---|---|---|---|---|---|
| 6 | OH | CH$_2$OH | H | OMe | H | H | epoxide |
| 7 | OH | CH$_2$OH | H | OH | H | OH | = |
| 8 | OH | CH$_2$OH | H | OH | H | OH | epoxide |
| 9 | OCMe$_2$OCH$_2$ | | H | OCOCH$_2$OBn | H | H | = |
| 10 | OH | CH$_2$OH | H | OCOCH$_2$OBn | H | H | = |
| 11 | OH | CH$_2$OTr | H | OH | H | H | = |
| 12 | OBn | CH$_2$OTr | H | OBn | H | H | = |
| 13 | OBn | CH$_2$OH | H | OBn | H | H | = |
| 14 | OBn | CHO | H | OBn | H | H | = |
| 15 | OBn | COOH | H | OBn | H | H | = |
| 16 | OBn | CONH$^n$Bu | H | OBn | H | H | = |
| 17 | OH | CONH$^n$Bu | H | OH | H | H | = |
| 18 | OH | CH$_2$OH | H | OCMe$_2$O | H | | = |
| 19 | OAc | CH$_2$OAc | H | OCMe$_2$O | H | | = |
| 20 | OAc | CH$_2$OAc | H | OH | H | OH | = |
| 21 | OMe | CH$_2$OMe | H | OCMe$_2$O | H | | = |
| 22 | OMe | CH$_2$OMe | H | OH | H | OH | = |
| 23 | OCH(Ph)OCH$_2$ | | H | OH | H | OH | = |
| 24 | OCH(Ph)OCH$_2$ | | H | OAc | H | OAc | = |
| 25 | OCH(Ph)OCH$_2$ | | H | OH | H | OAc | = |
| 26 | OH | CH$_2$OH | H | OAc | H | OAc | = |
| 27 | OH | CH$_2$OH | H | OH | H | OAc | = |
| 28 | OCH(Ph)OCH$_2$ | | H | OMe | H | OMe | = |
| 29 | OCH(Ph)OCH$_2$ | | H | OH | H | OMe | = |
| 30 | OCH(Ph)OCH$_2$ | | H | OMe | H | OH | = |
| 31 | OH | CH$_2$OH | H | OMe | H | OMe | = |
| 32 | OH | CH$_2$OH | H | OH | H | OMe | = |
| 33 | OH | CH$_2$OH | H | OMe | H | OH | = |
| 34 | OCH(Ph)OCH$_2$ | | | =O | | =O | = |
| 35 | OCH(Ph)OCH$_2$ | | | =O | H | OH | = |
| 36 | OH | CH$_2$OH | | =O | | =O | = |
| 37 | OH | CH$_2$OH | | =O | H | OH | = |
| 38 | OCH(Ph)OCH$_2$ | | OH | H | OH | H | = |
| 39 | OCH(Ph)OCH$_2$ | | H | OH | OH | H | = |
| 40 | OCH(Ph)OCH$_2$ | | OH | H | H | OH | = |
| 41 | OH | CH$_2$OH | H | OH | OH | H | = |
| 42 | OH | CH$_2$OH | OH | H | H | OH | = |
| 43 | OCH(Ph)OCH$_2$ | | | =O | H | OAc | = |
| 44 | OCH(Ph)OCH$_2$ | | H | OMs | H | OAc | = |
| 45 | OCH(Ph)OCH$_2$ | | H | H | H | OH | = |
| 46 | OH | CH$_2$OH | H | H | H | OH | = |
| 47 | OCH(Ph)OCH$_2$ | | H | H | | =O | = |
| 48 | OCH(Ph)OCH$_2$ | | H | H | OH | H | = |
| 49 | OH | CH$_2$OH | H | H | OH | H | = |
| 50 | OCMe$_2$OCH$_2$ | | H | OTs | H | H | = |
| 51 | OCMe$_2$OCH$_2$ | | H | = | | H | = |
| 52 | OH | CH$_2$OH | H | = | | H | = |
| 53 | OH | CH$_2$OH | H | H | H | H | = |
| 54 | OH | CH$_2$OTr | H | H | H | H | = |
| 55 | OCOPh | CH$_2$OTr | H | H | H | H | = |
| 56 | OCOPh | CH$_2$OH | H | H | H | H | = |

-continued

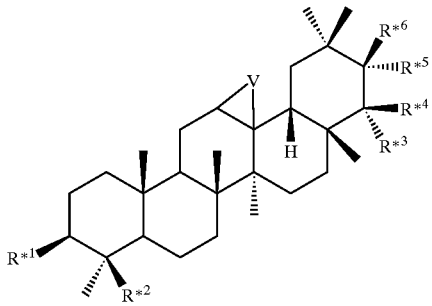

(A)

| compound | $R^{*1}$ | $R^{*2}$ | $R^{*3}$ | $R^{*4}$ | $R^{*5}$ | $R^{*6}$ | V |
|---|---|---|---|---|---|---|---|
| 57 | OCOPh | CHO | H | H | H | H | = |
| 58 | OH | CHO | H | H | H | H | = |
| 59 | OH | CH(OH)Me | H | H | H | H | = |
| 60 | OCOPh | COOH | H | H | H | H | = |
| 61 | OH | COOH | H | H | H | H | = |
| 62 | OH | COOMe | H | H | H | H | = |
| 63 | OH | COMe | H | H | H | H | = |
| 64 | OH | C(OH)Me$_2$ | H | H | H | H | = |
| 65 | OH | CH=CH$_2$ | H | H | H | H | = |
| 66 | OH | CH$_2$OH | H | H | H | =O | = |
| 67 | OCMe$_2$OCH$_2$ | | H | OCOCH$_2$CO$_2$Et | H | H | = |
| 68 | OH | CH$_2$OH | H | OCOCH$_2$CO$_2$H | H | H | = |
| 69 | OCMe$_2$OCH$_2$ | | H | O(CH$_2$)$_3$CO$_2$Me | H | H | = |
| 70 | OH | CH$_2$OH | H | O(CH$_2$)$_3$CO$_2$Me | H | H | = |
| 71 | OH | CH$_2$OH | H | O(CH$_2$)$_3$CO$_2$H | H | H | = |
| 72 | OCMe$_2$OCH$_2$ | | H | OCONHPh | H | H | = |
| 73 | OH | CH$_2$OH | H | OCONHPh | H | H | = |
| 74 | OH | CH$_2$OH | H | OCONH$_2$ | H | H | = |

Example 1

12α,13α-Epoxyoleanane-3β,22β,24(4β)-triol (compound 2)

Compound 1 (230 mg, 0.5 mmol) was dissolved in 10 ml of dichloromethane and 3 ml of chloroform, 216 mg of 50–60% m-chloroperoxybenzoic acid was added to the solution, and the mixture was stirred at room temperature overnight. The reaction solution was diluted with dichloromethane, washed with a saturated aqueous sodium bicarbonate solution and then with saturated saline, and dried over magnesium sulfate. The inorganic salt was removed by filtration, and the filtrate was concentrated under reduced pressure to obtain an oil which was then purified by column chromatography on silica gel (development system, n-hexane:ethyl acetate=1:1) to give 193 mg (yield: 81%) of compound 2 as a colorless solid.

$^1$H-NMR (CDCl$_3$) δppm 0.88 (3H, s), 0.90 (3H, s), 0.97 (3H, s), 0.98 (3H, s), 0.99 (3H, s), 1.04 (3H, s), 1.22 (3H, s), 0.74–1.87 (22H, m), 2.36 (1H, d, J=4.16 Hz), 2.76 (1H, dd, J=2.50 Hz, 9.16 Hz), 3.05 (1H, s), 3.29 (1H, t, J=10.5 Hz), 3.40–3.45 (1H, m), 3.55–3.60 (1H, m), 4.17 (1H, d, J=10.5 Hz) MS EI (m/z): 474 (M$^+$)

Example 2

3β,24(4β)-Isopropylidenedioxy-22β-methoxyolean-12-ene (compound 4)

Compound 3 (300 mg) was dissolved in 5 ml of THF, 130 mg of 55% sodium hydride was added to the solution, and the mixture was stirred at room temperature for 1 hr. Then 2 ml of methyl iodide was added, and the mixture was stirred overnight. The reaction solution was diluted with ethyl acetate, washed with water, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=10:1) to give 285 mg (yield: 93%) of compound 4 as a colorless foam.

$^1$H-NMR (CDCl$_3$) δppm 0.86 (3H, s), 0.90 (3H, s), 0.99 (3H, s), 1.00 (3H, s), 1.11 (3H, s), 1.15 (3H, s), 1.22 (3H, s), 1.37 (3H, s), 1.44 (3H, s), 0.83–2.10 (21H, m), 2.80–2.83 (1H, m), 3.23 (1H, d, J=11.8 Hz), 3.28 (3H, s), 3.44–3.47 (1H, m), 4.06 (1H, d, J=11.8 Hz), 5.23 (1H, t-like) MS FD (m/z): 512 (M$^+$)

Example 3

22β-Methoxyolean-12-ene-3β,24(4β)-diol (compound 5)

Compound 4 (280 mg) was dissolved in THF, 0.66 ml of boron trifluoride ethyl ether was added to the solution, and the mixture was stirred at room temperature for 1 hr. The reaction solution was neutralized with a saturated aqueous sodium hydrogencarbonate solution and extracted with ethyl acetate. The extract was dried over magnesium sulfate. The inorganic salt was removed by filtration, and the filtrate was concentrated under reduced pressure to obtain a concentrate which was then purified by column chromatography on silica gel (development system, n-hexane:ethyl acetate=2:1) to give 203 mg (yield: 79%) of compound 5 as a colorless solid.

¹H-NMR (CDCl₃) δppm 0.85 (3H, s), 0.89 (3H, s), 0.90 (3H, s), 0.94 (3H, s), 1.00 (3H, s), 1.11 (3H, s), 1.25 (3H, s), 0.80–2.10 (21H, m), 2.80–2.82 (1H, m), 3.28 (3H, s), 3.33 (1H, d, J=11.1 Hz), 3.42–3.45 (1H, m), 5.22 (1H, t-like) MS EI (m/z): 472 (M⁺)

Example 4

22β-Methoxy-12,13-epoxyoleanane-3β,24(4β)-diol (compound 6)

Compound 5 (50 mg, 0.1 mmol) was dissolved in 1 ml of dichloromethane, 31 mg of 70% m-chloroperoxybenzoic acid was added to the solution, and the mixture was stirred at room temperature overnight. The reaction solution was diluted with dichloromethane, washed with a saturated aqueous sodium bicarbonate solution and then with saturated saline, and dried over magnesium sulfate. The inorganic salt was removed by filtration, and the filtrate was concentrated under reduced pressure to obtain a solid which was then purified by column chromatography on silica gel (development system, n-hexane:ethyl acetate=1:1) to give 14.5 mg (yield: 28%) of compound 6 as a colorless solid.

¹H-NMR (CDCl₃) δppm 0.87 (3H, s), 0.89 (3H, s), 0.96 (3H, s), 0.97 (3H, s), 0.99 (3H, s), 1.04 (3H, s), 1.22 (3H, s), 0.74–1.88 (21H, m), 2.42 (1H, br.s), 2.80 (1H, br.s), 2.94 (1H, dd, J=3.33 Hz, 9.71 Hz), 3.04 (1H, s), 3.26–3.30 (1H, m), 3.29 (3H, s), 3.40–3.44 (1H, m), 4.17 (1H, d, J=9.71 Hz) MS EI (m/z):488 (M⁺)

Example 5

12,13-Epoxyoleanane-3β,21β,22β,24(4β)-tetraol (compound 8)

Compound 7 (50 mg, 0.1 mmol) was dissolved in 1 ml of dichloromethane and 1 ml of chloroform, 32 mg of 70% m-chloroperoxybenzoic acid was added to the solution, and the mixture was stirred at 37° C. overnight. The reaction solution was diluted with dichloromethane, washed with a saturated aqueous sodium bicarbonate solution and then with saturated saline, and dried over magnesium sulfate. The inorganic salt was removed by filtration, and the filtrate was concentrated under reduced pressure to obtain a solid which was then purified by column chromatography on silica gel (development system, n-hexane:ethyl acetate=1:1) to give 18 mg (yield: 35%) of compound 8 as a colorless solid.

¹H-NMR (CDCl₃) δppm 0.89 (3H, s), 0.91 (3H, s), 1.00 (3H, s), 1.05 (3H, s), 1.13 (3H, s), 1.14 (3H, s), 1.23 (3H, s), 0.75–2.08 (23H, m), 3.03 (1H, s), 3.28 (1H, d, J=11.28 Hz), 3.40–3.51 (3H, m), 4.17 (1H, d, J=11.28 Hz) MS FAB (m/z): 491 (M⁺+1)

Example 6

22β-Benzyloxyacetyloxy-3β,24(4β)-isopropylidenedioxyolean-12-ene (compound 9)

Compound 3 (38 mg) was dissolved in 5 ml of dichloromethane, 15 mg of 4-dimethylaminopyridine and 18 μl of benzyloxyacetyl chloride were added to the solution, and the mixture was stirred at room temperature for 1.5 hr. The reaction solution was diluted with dichloromethane, washed with water, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=3:1) to give 36 mg (yield: 76%) of compound 9 as a colorless foam.

¹H-NMR (CDCl₃) δppm 0.81 (3H, s), 0.90 (3H, s), 0.96 (3H, s), 0.98 (3H, s), 1.14 (3H, s), 1.15 (3H, s), 1.22 (3H, s), 1.38 (3H, s), 1.44 (3H, s), 0.87–2.20 (21H, m), 3.23 (1H, d, J=11.65 Hz), 3.46 (1H, dd, J=4.44 Hz, 11.44 Hz), 4.03–4.10 (3H, m), 4.64 (2H, d, J=1.94 Hz), 4.78 (1H, t-like), 5.25 (1H, t-like), 7.30–7.39 (5H, m) MS FAB (m/z): 647 (M⁺+1)

Example 7

22β-Benzyloxyacetyloxyolean-12-ene-3β,24(4β)-diol (compound 10)

Compound 9 (36 mg) was dissolved in 1 ml of dichloromethane and 2 ml of methanol, 1 ml of hydrochloric acid was added to the solution, and the mixture was stirred at room temperature for 1 hr. The reaction solution was diluted with dichloromethane, washed with water, and dried over magnesium sulfate. The inorganic salt was removed by filtration, and the filtrate was concentrated under reduced pressure to give 30 mg (yield: 88%) of compound 10 as a colorless solid.

¹H-NMR (CDCl₃) δppm 0.80 (3H, s), 0.89 (3H, s), 0.90 (3H, s), 0.94 (3H, s), 0.96 (3H, s), 1.14 (3H, s), 1.25 (3H, s), 0.84–2.20 (21H, m), 3.35 (1H, d, J=11.1 Hz), 3.42–3.47 (1H, m), 4.10 (2H, dd, J=16.37 Hz, 26.91 Hz), 4.20 (1H, d, J=11.1 Hz), 4.64 (2H, d, J=1.67 Hz), 4.78 (1H, t-like), 5.24 (1H, t-like), 7.28–7.38 (5H, m) MS EI (m/z): 606 (M⁺)

Example 8

3β,22β-Dibenzyloxy-24(4β)-triphenylmethyloxyolean-12-ene (compound 12)

Compound 11 (95 mg) was dissolved in 5 ml of anhydrous DMF, 83 mg of 60% sodium hydride was added to the solution, and the mixture was stirred at room temperature for 1.5 hr. Thereafter, 75 μl of benzyl bromide was added to the reaction mixture, and the mixture was stirred at 40° C. for 5 hr. The reaction mixture was diluted with ethyl acetate, washed thrice with water, and dried over magnesium sulfate. The inorganic salt was removed by filtration, and the filtrate was concentrated under reduced pressure to obtain an oil which was then purified by column chromatography on silica gel (development system, n-hexane:ethyl acetate= 10:1) to give 118 mg (yield: 65%) of compound 12 as a colorless solid.

¹H-NMR (CDCl₃) δppm 0.33 (3H, s), 0.82 (3H, s), 0.88 (3H, s), 0.92 (3H, s), 1.03 (3H, s), 1.08 (3H, s), 1.34 (3H, s), 0.70–2.15 (21H, m), 2.93–2.97 (1H, m), 3.06–3.07 (1H, m), 3.17 (1H, d, J=9.2 Hz), 3.53 (1H, d, J=9.2 Hz), 4.32 (1H, d, J=11.9 Hz), 4.38 (1H, d, J=11.9 Hz), 4.61 (1H, d, J=11.9 Hz), 4.63 (1H, d, J=11.9 Hz), 5.17 (1H, t-like), 7.19–7.50 (25H, m) MS FD (m/z): 881 (M⁺+1)

Example 9

3β,22β-Dibenzyloxyolean-12-en-24(4β)-ol (compound 13)

Compound 12 (440 mg) was dissolved in 10 ml of methanol and 2 ml of acetone. Concentrated hydrochloric acid (0.4 ml) was added to the solution, and the mixture was refluxed for 30 min. Water was added to the reaction solution, and the mixture was then neutralized with 1 N sodium hydroxide and extracted thrice with methylene chloride. The organic layer was dried over magnesium sulfate, the inorganic salt was removed by filtration, and the filtrate was concentrated under reduced pressure to obtain an oil which was then purified by column chromatography on silica gel (development system, n-hexane:ethyl acetate= 10:1) to give 231 mg (yield: 72%) of compound 13 as an oil.

$^1$H-NMR(CDCl$_3$) δppm 0.88 (3H, s), 0.89 (3H, s), 0.93 (3H, s), 0.94 (3H, s), 1.05 (3H, s), 1.11 (3H, s), 1.21 (3H, s), 0.85–2.18 (22H, m), 3.07–3.08 (1H, m), 3.18–3.24 (2H, m), 4.16 (1H, d, J=10.5 Hz), 4.32 (1H, d, J=11.7 Hz), 4.39 (1H, d, J=11.7 Hz), 4.62 (1H, d, J=11.7 Hz), 4.67 (1H, d, J=11.7 Hz), 5.22 (1H, t-like), 7.26–7.34 (10H, m) MS SIMS (m/z): 639 (M$^+$+1)

Example 10

3β,22β-Dibenzyloxy-24(4β)-oxolean-12-ene (compound 14)

Oxalyl chloride (0.15 ml) was dissolved in 4 ml of methylene chloride, and the solution was cooled to −78° C. A solution of 0.23 ml of DMSO in methylene chloride was added to the cooled solution, and the mixture was stirred for 10 min. A solution of 128 mg of compound 13 in 2 ml of methylene chloride was added to the reaction solution thus prepared, and the mixture was stirred at −78° C. for 15 min. To the reaction solution was added 0.7 ml of triethylamine, and the mixture was stirred at −78° C. for 5 min. The temperature of the reaction solution was gradually raised to 0° C. The reaction solution was diluted with water, extracted with methylene chloride, washed with saturated sodium hydrogencarbonate, and dried over anhydrous magnesium sulfate. The inorganic salt was removed by filtration, the filtrate was concentrated under reduced pressure, and the resultant oil was purified by column chromatography on silica gel (development system, n-hexane:ethyl acetate= 10:1) to give 104 mg (yield: 82%) of compound 14 as a colorless foam substance.

$^1$H-NMR (CDCl$_3$) δppm 0.83 (3H, s), 0.89 (3H, s), 0.93 (3H, s), 0.94 (3H, s), 1.04 (3H, s), 1.10 (3H, s), 1.21 (3H, s), 0.85–2.18 (21H, m), 3.07 (1H, dd, J=3.1 Hz, 3.1 Hz), 3.18 (1H, dd, J=5.1 Hz, 5.1 Hz), 4.20, 4.61 (1H, each, both d, J=11.7 Hz), 5.23 (1H, t-like), 7.22–7.35 (10H, m), 10.07 (1H, s) MS SIMS (m/z): 637 (M$^+$+1)

Example 11

3β,22β-Dibenzyloxyolean-12-en-24(4β)-oic acid (compound 15)

Compound 14 (20 mg) was dissolved in 6 ml of tert-butanol, and 1.5 ml of 2-methyl-2-butene was added to the solution. A solution of 250 mg of sodium chlorite and 250 mg of monosodium phosphate in 2.5 ml of water was added to the reaction solution, and the mixture was then stirred at room temperature overnight. The reaction solution was concentrated under reduced pressure and extracted with ethyl acetate, and the extract was dried over magnesium sulfate. The inorganic salt was removed by filtration, and the filtrate was concentrated under reduced pressure to obtain an oil which was then purified by column chromatography on silica gel (development system, n-hexane:ethyl acetate=5:1) to give 6.8 mg (yield: 34%) of compound 15 as a colorless solid.

$^1$H-NMR (CDCl$_3$) δppm 0.89 (3H, s), 0.94 (3H, s), 0.95 (3H, s), 1.02 (3H, s), 1.04 (3H, s), 1.10 (3H, s), 1.40 (3H, s), 0.85–2.19 (21H, m), 3.05–3.09 (1H, m), 3.15–3.19 (1H, m), 4.32 (1H, d, J=11.83 Hz), 4.56 (1H, d, J=11.83 Hz), 4.61 (1H, d, J=11.83 Hz), 4.85 (1H, d, J=11.83 Hz), 5.23 (1H, t-like), 7.23–7.52 (10H, m). MS EI (m/z): 652 (M$^+$)

Example 12

N-n-Butyl-3β,22β-dibenzyloxyolean-12-en-24(4β)-oic amide (compound 16)

Compound 15 (20 mg) was dissolved in 1 ml of anhydrous DMF. BOP reagent (16 mg) was added to the solution, and the mixture was stirred at room temperature for 2 hr. n-Butylamine (0.1 ml) was added to the reaction solution, and the mixture was stirred at room temperature for 1 hr. The reaction solution was diluted with ethyl acetate, washed twice with water, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=5:1) to give 16 mg (yield: 73%) of compound 16 as a colorless foam.

$^1$H-NMR (CDCl$_3$) δppm 0.89 (3H, s), 0.92 (3H, s), 0.93 (3H, s), 1.01 (3H, s), 1.04 (3H, s), 1.10 (3H, s), 1.34 (3H, s), 0.82–2.25 (28H, m), 3.08–3.18 (4H, m), 4.32 (1H, d, J=11.65 Hz), 4.46 (1H, d, J=11.65 Hz), 4.61 (1H, d, J=11.65 Hz), 4.75 (1H, d, J=11.65 Hz), 5.23 (1H, t-like), 7.28–7.37 (10H, m), 7.50 (1H, t-like) MS FAB (m/z): 708 (M$^+$+1)

Example 13

N-n-Butyl-3β,22β-dihydroxyolean-12-en-24(4β)-oic amide (compound 17)

Compound 16 (13 mg) was dissolved in 1 ml of methanol and 1 ml of dichloromethane, and 13 mg of 10% Pd—C was added to the solution. The mixture was catalytically reduced at room temperature under atmospheric pressure for 2 hr. The reaction solution was filtered through Celite, and the filtrate was concentrated under reduced pressure to give 10 mg (yield: 100%) of compound 17 as a colorless solid.

$^1$H-NMR (CDCl$_3$) δppm 0.87 (3H, s), 0.90 (3H, s), 0.92 (3H, s), 1.02 (3H, s), 1.04 (3H, s), 1.12 (3H, s), 1.38 (3H, s), 0.91–2.22 (29H, m), 3.10–3.25 (3H,m),3.40–3.45 (1H, m), 3.77 (1H, d, J=8.75 Hz), 5.27 (1H, t-like), 5.97 (1H, t-like) MS EI (m/z): 527 (M$^+$)

Example 14

3β,24(4β)-Diacetoxy-21β,22β-isopropylidenedioxyolean-12-ene (compound 19)

21β,22β-Isopropylidenedioxyolean-12-ene-3β,24(4β)-diol (compound 18) (20 mg) was dissolved in 0.5 ml of anhydrous pyridine, 0.5 ml of anhydrous acetic acid was added to the solution, and the mixture was stirred at room temperature overnight. Ice water was added to the reaction solution, extracted with ethyl acetate, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=3:1) to give 19 mg (yield: 80%) of compound 19 as a colorless solid.

$^1$H-NMR (CDCl$_3$) δppm 0.92 (3H, s), 0.98 (9H, s), 1.00 (3H, s), 1.03 (3H, s), 1.11 (3H, s), 1.34 (3H, s), 1.49 (3H, s), 2.04 (3H, s), 2.07 (3H, s), 1.00–2.28 (19H, m), 3.73 (2H, s), 4.14 (1H, d, J=11.5 Hz), 4.37 (1H, d, J=11.5 Hz), 4.57–4.61 (1H, m), 5.27 (1H, t-like) MS EI (m/z): 598 (M$^+$)

Example 15

3β,24(4β)-Diacetoxyolean-12-ene-21β,22β-diol (compound 20)

Compound 19 (18 mg) was dissolved in 0.5 ml of dichloromethane and 1 ml of methanol, 0.2 ml of 1 N hydrochloric acid was added to the solution, and the mixture was stirred at room temperature for 2 hr. The reaction solution was diluted with dichloromethane, washed with water, and dried over magnesium sulfate. The inorganic salt was removed by filtration, and the filtrate was concentrated under reduced pressure to obtain a concentrate which was then purified by column chromatography on silica gel (development system, dichloromethane:ethyl acetate=3:1) to give 14 mg (yield: 79%) of compound 20 as a colorless solid.

$^1$H-NMR (CDCl$_3$) δppm 0.96 (3H, s), 0.97 (3H, s), 0.98 (6H, s), 1.02 (3H, s), 1.03 (3H, s), 1.15 (3H, s), 2.02 (3H, s), 2.04 (3H, s), 0.99–2.27 (21H, m), 3.41 (1H, t, J 3.6 Hz), 3.51 (1H, dd, J=3.6 Hz, 7.5 Hz), 4.14 (1H, d, J=11.7 Hz), 4.37 (1H, d, J=11.7 Hz), 4.56–4.61 (1H, m), 5.26 (1H, t-like) MS FAB (m/z):581 (M+Na$^+$)

Example 16

3β,24(4β)-Dimethoxyolean-12-ene-21β,22β-diol (compound 22)

21β,22β-Isopropylidenedioxy-3β,24(4β)-dimethoxyolean-12-ene (compound 21) (15 mg) was dissolved in 1 ml of dichloromethane and 1 ml of methanol, 0.2 ml of 1 N hydrochloric acid was added to the solution, and the mixture was stirred at room temperature for 1.5 hr. The reaction solution was diluted with dichloromethane, washed with water, and dried over magnesium sulfate. The inorganic salt was removed by filtration, and the filtrate was concentrated under reduced pressure to give 12 mg (yield: 87%) of compound 22 as a colorless solid.

$^1$H-NMR (CDCl$_3$) δppm 0.97 (6H, s), 0.99 (3H, s), 1.00 (3H, s), 1.02 (3H, s), 1.12 (3H, s), 1.14 (3H, s), 0.73–2.26 (21H, m), 2.72 (1H, dd, J=4.2 Hz, 11.9 Hz), 3.27 (3H, s), 3.31 (1H, d, J=9.7 Hz), 3.35 (3H, s), 3.41 (1H, t, J=3.6 Hz), 3.51 (1H, dd, J=3.6 Hz, 7.5 Hz), 3.54 (1H, d, J=9.7 Hz), 5.27 (1H, t-like) MS EI (m/z): 502 (M$^+$)

Example 17

3β,24(4β)-Benzylidenedioxyolean-12-ene-21β,22β-diol (compound 23)

Soyasapogenol A (compound 7) (1.0 g) was dissolved in 10 ml of anhydrous DMF, and 0.38 ml of benzaldehyde dimethyl acetal and 10 mg of camphorsulfonic acid were added to the solution, and the mixture was stirred at room temperature overnight. The reaction solution was diluted with ethyl acetate, washed with a saturated sodium hydrogencarbonate solution, and dried over magnesium sulfate. The inorganic salt was removed by filtration, and the filtrate was concentrated under reduced pressure to obtain a concentrate which was then purified by column chromatography on silica gel (development system, n-hexane:ethyl acetate= 2:1) to give 728 mg (yield: 61%) of compound 23 as a colorless solid.

$^1$H-NMR (CDCl$_3$) δppm 0.96 (3H, s), 0.97 (3H, s), 1.00 (3H, s), 1.02 (3H, s), 1.08 (3H, s), 1.17 (3H, s), 1.48 (3H, s), 0.90–2.47 (21H, m), 3.42 (1H, br s), 3.51 (1H, br s), 3.62 (1H, d, J=11.0 Hz), 3.64 (1H, dd, J=5.4 Hz, 12.1 Hz), 4.31 (1H, d, J=11.0 Hz), 5.27 (1H, t-like), 5.78 (1H, s), 7.32–7.39 (3H, m), 7.49–7.52 (2H, m) MS FAB (m/z): 585 (M+Na$^+$)

Example 18

21β,22β-Diacetoxy-3β,24(4β)-benzylidenedioxyolean-12-ene (compound 24) and

21β-Acetoxy-3β,24(4β)-benzylidenedioxyolean-12-en-22β-ol (compound 25)

Compound 23 (100 mg) was dissolved in 2.5 ml of anhydrous pyridine, 1 ml of anhydrous acetic acid was added to the solution, and the mixture was stirred at room temperature for 3 hr. Ice water was added to the reaction solution, extracted with ethyl acetate, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=3:1) to give 23 mg (yield: 20%) of compound 24 and 69 mg (yield 65%) of compound 25 as colorless solids.

$^1$H-NMR (CDCl$_3$) δppm (compound 24) 0.80 (3H, s), 0.88 (3H, s), 0.97 (3H, s), 1.07 (3H, s), 1.08 (3H, s), 1.18 (3H, s), 1.48 (3H, s), 2.00 (3H, s), 2.07 (3H, s), 0.89–2.47 (19H, m), 3.62 (1H, d, J=11.0 Hz), 3.64 (1H, dd, J=5.1 Hz, 12.1 Hz), 4.30 (1H, d, J=11.0 Hz), 4.90 (2H, s), 5.29 (1H, t-like), 5.78 (1H, s), 7.30–7.39 (3H, m), 7.49–7.52 (2H, m) MS EI (m/z): 647 (M+H)$^+$ $^1$H-NMR (CDCl$_3$) δppm (compound 25) 0.87 (3H, s), 0.97 (3H, s), 1.00 (3H, s), 1.08 (3H, s), 1.13 (3H, s), 1.18 (3H, s), 1.49 (3H, s), 2.14 (3H, s), 0.90–2.48 (20H, m), 3.46 (1H, d, J=3.1 Hz), 3.62 (1H, d, J=11.3 Hz), 3.65 (1H, dd, J=5.9 Hz, 12.8 Hz), 4.31 (1H, d, J=11.3 Hz), 4.94 (1H, d, J=3.1 Hz), 5.28 (1H, t-like), 5.79 (1H, s), 7.28–7.39 (3H, m), 7.49–7.52 (2H, m) MS EI (m/z): 604 (M$^+$)

Example 19

21β,22β-Diacetoxyolean-12-ene-3β,24(4β)-diol (compound 26)

Compound 24 (23 mg) was dissolved in 1 ml of methanol and 1 ml of dichloromethane, and 5 mg of 10% Pd—C was added to the solution. The mixture was catalytically reduced at room temperature under atmospheric pressure for 4 hr. The reaction solution was filtered through Celite, and the filtrate was concentrated under reduced pressure to give 16 mg (yield: 82%) of compound 26 as a colorless solid.

$^1$H-NMR (CDCl$_3$) δppm 0.79 (3H, s), 0.87 (3H, s), 0.89 (3H, s), 0.94 (3H, s), 1.07 (3H, s), 1.16 (3H, s), 1.25 (3H, s), 0.83–1.98 (18H, m), 2.00 (3H, s), 2.06 (3H, s), 2.23–2.28 (1H, m), 2.48 (1H, br s), 2.72 (1H, br s), 3.32–3.38 (1H, m), 3.45 (1H, dd, J=5.4 Hz, 12.1 Hz), 4.20 (1H, d, J=11.1 Hz), 4.89 (2H, s), 5.27 (1H, t-like), MS EI (m/z): 558 (M$^+$)

Example 20

21β-Acetoxyolean-12-ene-3β,22β,24(4β)triol (compound 27)

Compound 25 (20 mg) was dissolved in 1 ml of methanol and 1 ml of dichloromethane, and 5 mg of 10% Pd—C was added to the solution. The mixture was catalytically reduced at room temperature under atmospheric pressure for 1 hr. The reaction solution was filtered through Celite, and the filtrate was concentrated under reduced pressure to give 13 mg (yield: 79%) of compound 27 as a colorless solid.

$^1$H-NMR (CDCl$_3$) δppm 0.85 (3H, s), 0.89 (3H, s), 0.96 (6H, s), 1.12 (3H, s), 1.15 (3H, s), 1.25 (3H, s), 0.84–1.98 (19H, m), 2.13 (3H, s), 2.28–2.34 (1H, m), 2.43 (1H, br s), 2.71 (1H, br s), 3.32–3.50 (3H, m), 4.21 (1H, d, J=11.1 Hz), 4.93 (1H, d, J=3.3 Hz), 5.26 (1H, t-like), MS FAB (m/z): 539 (M+Na$^+$)

Example 21

3β,24(4β)-Benzylidenedioxy-21β,22β-dimethoxyolean-12-ene (compound 28),

3β,24(4β)-Benzylidenedioxy-22β-methoxyolean-12-en-21β-ol (compound 29), and

3β,24(4β)-Benzylidenedioxy-21β-methoxyolean-12-en-22β-ol (compound 30)

Compound 23 (20 mg) was dissolved in anhydrous THF, 14 mg of 60% sodium hydride was added to the solution, and the mixture was stirred at room temperature for 1 hr. Thereafter, 32 μl of methyl iodide was added to the reaction mixture, and the mixture was stirred for 6 hr. Water was added to the reaction solution, and the mixture was extracted with ethyl acetate. The extract was dried over magnesium sulfate. The inorganic salt was removed by filtration, and the filtrate was concentrated under reduced pressure to obtain a concentrate which was then purified by column chromatography on silica gel (development system, n-hexane:ethyl acetate=3:1) to give 6 mg (yield: 28%) of compound 28, 5 mg (yield: 26%) of compound 29, and 3 mg (yield: 14%) of compound 30 as a colorless solid.

$^1$H-NMR (CDCl$_3$) δppm (compound 28) 0.94 (6H, s), 0.99 (3H, s), 1.03 (3H, s), 1.07 (3H, s), 1.15 (3H, s), 1.48 (3H, s), 0.88–2.47 (19H, m), 3.02 (2H, br s), 3.43 (3H, s), 3.46 (3H, s), 3.62 (1H, d, J=11.5 Hz), 3.64 (1H, dd, J=5.7 Hz, 12.1 Hz), 4.31 (1H, d, J=11.5 Hz), 5.24 (1H, t-like), 5.78 (1H, s), 7.32–7.39 (3H, m), 7.49–7.52 (2H, m) MS EI (m/z): 590 (M$^+$)

$^1$H-NMR (CDCl$_3$) δppm (compound 29) 0.95 (3H, s), 1.00 (3H, s), 1.01 (3H, s), 1.03 (3H, s), 1.08 (3H, s), 1.16 (3H, s), 1.48 (3H, s), 0.90–2.48 (20H, m), 2.99 (1H, d, J=3.3 Hz), 3.40 (3H, s), 3.57 (1H, d, J=3.3 Hz), 3.62 (1H, d, J=11.1 Hz), 3.64 (1H, dd, J=5.6 Hz, 12.1 Hz), 4.30 (1H, d, J=11.1 Hz), 5.27 (1H, t-like), 5.79 (1H, s), 7.31–7.38 (3H, m), 7.49–7.52 (2H, m) MS EI (m/z): 576 (M$^+$)

$^1$H-NMR (CDCl$_3$) δppm (compound 30) 0.92 (3H, s), 0.95 (3H, s), 0.96 (3H, s), 0.99 (3H, s), 1.08 (3H, s), 1.15 (3H, s), 1.48 (3H, s), 0.90–2.46 (20H, m), 2.91 (1H, d, J=3.9 Hz), 3.44 (1H, d, J=3.9 Hz), 3.47 (3H, s), 3.62 (1H, J=10.8 Hz), 3.64 (1H, dd, J=5.4 Hz, 12.1 Hz), 4.30 (1H, d, J=10.8 Hz), 5.24 (1H, t-like), 5.78 (1H, s), 7.31–7.38 (3H, m), 7.49–7.52 (2H, m) MS EI (m/z): 576 (M$^+$)

Example 22

21β,22β-Dimethoxyolean-12-ene-3β,24(4β)-diol (compound 31)

Compound 28 (20 mg) was dissolved in 1 ml of methanol and 1 ml of dichloromethane, and 5 mg of 10% Pd—C was added to the solution. The mixture was catalytically reduced at room temperature under atmospheric pressure for 1 hr. The reaction solution was filtered through Celite, and the filtrate was concentrated under reduced pressure to give 15 mg (yield: 89%) of compound 31 as a colorless solid.

$^1$H-NMR (CDCl$_3$) δpp 0.89 (3H, s), 0.93 (6H, s), 0.95 (3H, s), 1.02 (3H, s), 1.13 (3H, s), 1.25 (3H, s), 0.83–1.88 (18H, m), 2.18–2.21 (1H, m), 2.41 (1H, br s), 2.74 (1H, br s), 3.01 (2H, s), 3.32–3.50 (2H, m), 3.42 (3H, s), 3.45 (3H, s), 4.21 (1H, d, J=11.3 Hz), 5.22 (1H, t-like), MS EI (m/z): 502 (M$^+$)

Example 23

22β-Methoxyolean-12-ene-3β,21β,24(4β)-triol (compound 32)

Compound 29 (13 mg) was dissolved in 1 ml of methanol and 1 ml of dichloromethane, and 5 mg of 10% Pd—C was added to the solution. The mixture was catalytically reduced at room temperature under atmospheric pressure for 2.5 hr. The reaction solution was filtered through Celite, and the filtrate was concentrated under reduced pressure to give 7 mg (yield: 68%) of compound 32 as a colorless solid.

$^1$H-NMR (CDCl$_3$) δppm 0.89 (3H, s), 0.94 (3H, s), 0.96 (3H, s), 0.99 (3H, s), 1.02 (3H, s), 1.14 (3H, s), 1.25 (3H, s), 0.82–1.89 (19H, m), 2.25–2.31 (2H, m), 2.41 (1H, br s), 2.73 (1H, br s), 2.98 (1H, d, J=3.3 Hz), 3.32–3.37 (1H, m), 3.40 (3H, s), 3.42–3.48 (1H, m), 3.56 (1H, d, J=3.3 Hz), 4.21 (1H, d, J=11.1 Hz), 5.24 (1H, t-like), MS EI (m/z): 488 (M$^+$)

Example 24

21β-Methoxyolean-12-ene-3β,22β,24(4β)-triol (compound 33)

Compound 30 (8 mg) was dissolved in 1 ml of methanol and 1 ml of dichloromethane, and 5 mg of 10% Pd—C was added to the solution. The mixture was catalytically reduced at room temperature under atmospheric pressure for 1 hr. The reaction solution was filtered through Celite, and the filtrate was concentrated under reduced pressure to give 6 mg (yield: 80%) of compound 33 as a colorless solid.

$^1$H-NMR (CDCl$_3$) δppm 0.89 (3H, s), 0.91 (3H, s), 0.94 (3H, s), 0.95 (3H, s), 0.95 (3H, s), 1.13 (3H, s), 1.25 (3H, s), 0.82–2.18 (20H, m), 2.41 (1H, br s), 2.73 (1H, br s), 2.90 (1H, d, J=4.0 Hz), 3.32–3.46 (3H, m), 3.46 (3H, s), 4.21 (1H, d, J=11.1 Hz), 5.22 (1H, t-like), MS EI (m/z): 488 (M$^+$)

Example 25

3β,24(4β)-Benzylidenedioxy-21,22-dioxolean-12-ene (compound 34) and

3β,24(4β)-Benzylidenedioxy-22-oxolean-12-en-21β-ol (compound 35)

Oxalyl chloride (0.15 ml) was dissolved in 4 ml of dichloromethane, and the solution was cooled to –78° C. A solution of 0.25 ml of DMSO in 1 ml of dichloromethane was added to the cooled solution, and the mixture was stirred for 10 min. A solution of 200 mg of compound 23 in 4 ml of dichloromethane was dropwise added to the reaction solution, and the mixture was stirred at –78° C. for 15 min. To the reaction solution was added 0.74 ml of triethylamine, and the mixture was stirred at –78° C. for 5 min. The temperature of the reaction solution was gradually raised to 0° C. Water was added thereto, the mixture was extracted with dichloromethane, and the extract was washed with saturated saline and dried over magnesium sulfate. The inorganic salt was removed by filtration, the filtrate was concentrated under reduced pressure to obtain a concentrate which was then purified by column chromatography on silica gel (development system, dichloromethane) to give 76 mg (yield: 37%) of compound 34 and 30 mg (yield: 15%) of compound 35 as yellow solid.

$^1$H-NMR (CDCl$_3$) δppm (compound 34) 0.98 (3H, s), 1.09 (3H, s), 1.14 (3H, s), 1.15 (3H, s), 1.16 (3H, s), 1.20 (3H, s), 1.49 (3H, s), 0.90–2.63 (19H, m), 3.62 (1H, d, J=11.1 Hz), 3.64 (1H, dd, J=5.3 Hz, 11.4 Hz), 4.29 (1H, d, J=11.1 Hz), 5.41 (1H, t-like), 5.78 (1H, s), 7.31–7.39 (3H, m), 7.49–7.52 (2H, m) MS EI (m/z): 558 (M$^+$)

$^1$H-NMR (CDCl$_3$) δppm (compound 35) 0.70 (3H, s), 0.97 (3H, s), 1.06 (3H, s), 1.09 (3H, s), 1.12 (3H, s), 1.27 (3H, s), 1.49 (3H, s), 0.91–2.49 (19H, m), 3.60–3.68 (3H, m), 4.19 (1H, d, J=4.2 Hz), 4.30 (1H, d, J=11.1 Hz) 5.32 (1H, t-like), 5.79 (1H, s), 7.30–7.40 (3H, m), 7.48–7.52 (2H, m) MS EI (m/z): 560 (M$^+$)

Example 26

21,22-Dioxolean-12-ene-3β,24(4β)-diol (compound 36)

Compound 34 (25 mg) was dissolved in 1 ml of dichloromethane and 2 ml of methanol, 0.5 ml of 1 N hydrochloric acid was added to the solution, and the mixture was stirred at room temperature for 4 hr. The reaction solution was diluted with dichloromethane, washed with water, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=1:1) to give 12 mg (yield: 59%) of compound 36 as a colorless solid.

$^1$H-NMR (CDCl$_3$) δppm 0.91 (3H, s), 0.94 (3H, s), 1.13 (3H, s), 1.14 (3H, s), 1.15 (3H, 5), 1.18 (3H, s), 1.25 (3H, s), 0.80–2.75 (21H, m), 3.32–3.39 (1H, m), 3.41–3.49 (1H, m) ,4.21 (1H, d, J=11.0 Hz), 5.40 (1H, t-like), MS FAB (m/z): 471 (M+H)$^+$

Example 27

22-Oxolean-12-ene-3β,21β,24(4β)-triol (compound 37)

Compound 35 (25 mg) was dissolved in 1 ml of dichloromethane and 2 ml of methanol, 0.5 ml of 1 N hydrochloric acid was added to the solution, and the mixture was stirred at room temperature for 4 hr. The reaction solution was diluted with dichloromethane, washed with water, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=1:1) to give 13 mg (yield: 61%) of compound 37 as a colorless solid.

$^1$H-NMR (CDCl$_3$) δppm 0.69 (3H, s), 0.90 (3H, s), 0.94 (3H, s), 1.05 (3H, s), 1.11 (3H, s), 1.25 (3H, s), 1.26 (3H, s), 0.80–2.73 (21H, m), 3.32–3.38 (1H, m), 3.42–3.49 (1H, m), 3.65 (1H, d, J=4.1 Hz), 4.18 (1H, d, J=4.1 Hz), 4.21 (1H, d, J=11.2 Hz), 5.30 (1H, t-like), MS FAB (m/z): 473 (M+H)$^+$

Example 28

3β,24(4β)-Benzylidenedioxyolean-12-ene-21β,22β-diol (compound 23),

3β,24(4β)-Benzylidenedioxyolean-12-ene-21α,22α-diol (compound 38),

3β,24(4β)-Benzylidenedioxyolean-12-ene-21α,22β-diol (compound 39), and

3β,24(4β)-Benzylidenedioxyolean-12-ene-21β,22α,-diol (compound 40)

Lithium aluminum hydride (30 mg) was suspended in 3 ml of anhydrous THF. A solution of compound 34 (193 mg) in 2 ml of anhydrous THF was dropwise added to the solution under ice cooling, and the mixture was stirred for 2 hr. A saturated sodium sulfate was added to the reaction solution and stirred at room temperature for a while. The insoluble was removed by filtration, the filtrate was concentrated under reduced pressure to obtain a concentrate which was then purified by column chromatography on silica gel (development system, n-hexane:THF=3:1) to give 89 mg (yield: 46%) of a compound 23/compound 38 mixture, 11 mg (yield: 5%) of compound 39, and 8 mg (yield: 4%) of compound 40.

$^1$H-NMR (CDCl$_3$) δppm (compound 39) 0.85 (3H, s), 0.89 (3H, s), 0.95 (3H, s), 1.08 (6H, s), 1.10 (3H, s), 1.48 (3H, s), 0.85–2.48 (21H, m), 3.21–3.44 (2H, m), 3.60–3.68 (2H, m), 4.30 (1H, d, J=11.3 Hz), 5.30 (1H, t-like), 5.78 (1H, s), 7.31–7.40 (3H, m), 7.48–7.53 (2H, m) MS FAB (m/z): 585 (M+Na$^+$)

$^1$H-NMR (CDCl$_3$) δppm (compound 40) 0.91 (3H, s), 0.97 (3H, s), 1.00 (3H, s), 1.01 (3H, s), 1.07 (3H, s), 1.16 (3H, s), 1.48 (3H, s), 0.85–2.48 (21H, m), 3.27–3.35 (2H, m), 3.60–3.68 (2H,m), 4.30 (1H, d, J=11.3 Hz), 5.25 (1H, t-like), 5.78 (1H, s), 7.30–7.39 (3H, m), 7.48–7.52 (2H, m) MS FAB (m/z): 585 (M+Na$^+$)

Example 29

Olean-12-ene-3β,21α,22β,24(4β)-tetraol (compound 41)

Compound 39 (11 mg) was dissolved in 0.5 ml of dichloromethane and 1 ml of methanol, 0.1 ml of 1 N hydrochloric acid was added to the solution, and the mixture was stirred at room temperature for 4 hr. The reaction solution was diluted with dichloromethane, washed with water, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=1:1) to give 3 mg (yield: 34%) of compound 41 as a colorless solid.

$^1$H-NMR (CDCl$_3$) δppm 0.83 (3H, s), 0.87 (3H, s), 0.90 (3H, s), 0.91 (3H, s), 1.05 (3H, s), 1.08 (3H, s), 1.23 (3H, s), 0.85–2.27 (23H, m), 3.20–3.35 (3H, m), 3.40–3.46 (1H, m), 4.19 (1H, d, J=11.3 Hz), 5.26 (1H, t-like), MS EI (m/z): 474 (M$^+$)

Example 30

Olean-12-ene-3β,21β,22α,24(4β)-tetraol (compound 42)

Compound 40 (9 mg) was dissolved in 0.5 ml of dichloromethane and 1 ml of methanol, 0.1 ml of 1 N hydrochloric acid was added to the solution, and the mixture was stirred at room temperature for 4 hr. The reaction solution was diluted with dichloromethane, washed with water, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=1:1) to give 4 mg (yield: 58%) of compound 42 as a colorless solid.

$^1$H-NMR (CDCl$_3$) δppm 0.89 (3H, s), 0.90 (3H, s), 0.93 (3H, s), 0.99 (6H, s), 1.14 (3H, s), 1.25 (3H, s), 0.82–2.44 (21H, m), 3.00–3.05 (1H, m), 3.10–3.14 (1H, m), 3.22–3.47 (3H, m), 3.42 (1H, dd, J=6.6 Hz, 11.0 Hz), 4.20 (1H, d, J=11.0 Hz), 5.23 (1H, t-like), MS EI (m/z): 474 (M$^+$)

Example 31

21β-Acetoxy-3β,24(4β)-benzylidenedioxy-22-oxolean-12-ene (compound 43)

Compound 43 (49 mg, yield: 54%) was prepared from 91 mg of compound 25 in the same manner as in Example 18.

$^1$H-NMR (CDCl$_3$) δppm 0.86 (3H, s), 0.97 (3H, s), 1.03 (3H, s), 1.04 (3H, s), 1.08 (3H, s), 1.27 (3H, s), 1.49 (3H, s), 2.18 (3H, s), 0.90–2.49 (19H, m), 3.60–3.68 (2H,m), 4.30 (1H, d, J=11.3 Hz), 5.32 (2H, t-like), 5.78 (1H, s), 7.31–7.40 (3H, m), 7.48–7.52 (2H, m) MS EI (m/z): 602 (M$^+$)

Example 32

21β-Acetoxy-3β,24(4β)-benzylidenedioxy-22β-mesyloxyolean-12-ene (compound 44)

Compound 25 (316 mg) was dissolved in 8 ml of anhydrous pyridine, 162 μl of methane sulfonyl chloride and a catalytic amount of 4-DMAP were added to the solution, and the mixture was stirred at room temperature overnight. Ice water was added to the reaction solution, the mixture was extracted with ethyl acetate, and the extract was dried over magnesium sulfate. The inorganic salt was removed by filtration, and the filtrate was concentrated under reduced pressure to obtain a solid which was then washed with a mixed solution of n-hexane and ethyl acetate to give 331 mg (yield: 93%) of compound 44.

$^1$H-NMR (CDCl$_3$) δppm 0.91 (3H, s), 0.98 (3H, s), 1.00 (3H, s), 1.08 (3H, s), 1.10 (3H, s), 1.19 (3H, s), 1.49 (3H, s), 2.14 (3H, s), 0.93–2.48 (18H, m), 3.08 (3H, s), 3.60–3.68 (2H, m), 3.72–3.78 (1H, m), 4.30 (1H, d, J=11.5 Hz), 4.59 (1H, d, J=3.1 Hz), 4.97 (1H, d, J=3.1 Hz), 5.30 (1H, t-like), 5.78 (1H, s), 7.30–7.39 (3H, m), 7.49–7.52 (2H, m) MS TSP (m/z): 700 (M+NH$_4^+$)

Example 33

3β,24(4β)-Benzylidenedioxyolean-12-en-21β-ol (compound 45)

Triethylboronlithium hydride (1.0 M THF solution, 4.6 ml) was added to 315 mg of compound 44 under ice cooling, and the mixture was stirred at room temperature for 15 min. Water was added to the reaction solution, the mixture was extracted with ethyl acetate, and the extract was dried over magnesium sulfate. The inorganic salt was removed by filtration, and the filtrate was concentrated under reduced pressure to obtain a concentrate which was then purified by column chromatography on silica gel (development system, n-hexane:ethyl acetate=5:1) to give 221 mg (yield: 88%) of compound 45 as a foam substance.

$^1$H-NMR (CDCl$_3$) δppm 0.85 (3H, s), 0.94 (6H, s), 0.96 (3H, s), 1.08 (3H, s), 1.18 (3H, s), 1.48 (3H, s), 0.90–2.48 (22H, m), 3.47 (1H, br s), 3.62 (1H, d, J=11.3 Hz), 3.64 (1H, dd, J=5.1 Hz, 12.1 Hz), 4.30 (1H, d, J=11.3 Hz), 5.24 (1H, t-like), 5.78 (1H, s), 7.30–7.39 (3H, m), 7.49–7.52 (2H, m) MS TSP (m/z): 564 (M+NH$_4^+$)

Example 34

Olean-12-ene-3β,21β,24(4β)-triol (compound 46)

Compound 46 (18 mg, yield: 46%) as a colorless solid was prepared from 46 mg of compound 45 in the same manner as in Example 12.

$^1$H-NMR (CDCl$_3$) δppm 0.84 (3H, s), 0.89 (3H, s), 0.92 (3H, s), 0.93 (6H, s), 1.16 (3H, s), 1.24 (3H, s), 0.86–2.48 (24H, m), 3.33 (1H, d, J=11.3 Hz), 3.39–3.48 (2H, m) , 4.20 (1H, d, J=11.3 Hz), 5.22 (1H, t-like), MS TSP (m/z): 476 (M+NH$_4^+$)

Example 35

3β,24(4β)-Benzylidenedioxy-21-oxolean-12-ene (compound 47)

Compound 47 (56 mg, yield: 51%) as a colorless solid was prepared from 110 mg of compound 45 in the same manner as in Example 25.

1H-NMR (CDCl$_3$) δppm (compound 34) 0.96 (3H, s), 0.98 (3H, s), 1.02 (3H, s), 1.08 (3H, s), 1.13 (3H, s), 1.21 (3H, s), 1.48 (3H, s), 0.90–2.50 (21H, m), 3.62 (1H, d, J=11.3 Hz), 3.64 (1H, dd, J=4.9 Hz, 12.6 Hz), 4.30 (1H, d, J=11.3 Hz), 5.34 (1H, t-like), 5.79 (1H, s), 7.30–7.39 (3H, m), 7.49–7.53 (2H, m) MS FAB (m/z): 567 (M+Na$^+$)

Example 36

3β,24(4β)-Benzylidenedioxyolean-12-en-21α-ol (compound 48)

Compound 48 (11 mg, yield: 20%) as a colorless solid was prepared from 55 mg of compound 47 in the same manner as in Example 28.

$^1$H-NMR (CDCl$_3$) δppm (compound 34) 0.86 (3H, s), 0.87 (3H, s), 0.96 (3H, s), 0.97 (3H, s), 1.08 (3H, s), 1.14 (3H, s), 1.48 (3H, s), 0.90–2.48 (22H, m), 3.52 (1H, dd, J=4.6 Hz, 12.1 Hz), 3.62 (1H, d, J=11.0 Hz), 3.64 (1H, dd, J=5.1 Hz, 11.8 Hz), 4.30 (1H, d, J=11.0 Hz), 5.23 (1H, t-like), 5.78 (1H, s), 7.30–7.39 (3H, m), 7.49–7.53 (2H, m) MS FAB (m/z): 569 (M+Na$^+$)

Example 37

Olean-12-ene-3β,21α,24(4β)-triol (compound 49)

Compound 49 (7 mg, yield: 82%) as a colorless solid was prepared from 11 mg of compound 48 in the same manner as in Example 19.

$^1$H-NMR (CDCl$_3$+CD$_3$OD) δppm 0.85 (3H, s), 0.86 (3H, s), 0.89 (3H, s), 0.92 (6H, s), 0.96 (3H, s), 1.12 (3H, s); 1.23 (3H, s), 0.83–2.21 (21H, m), 3.32 (1H, d, J=11.0 Hz), 3.39–3.45 (1H, m), 3.50 (1H, dd, J=5.6 Hz, 11.8 Hz), 4.19 (1H, d, J=11.0 Hz), 5.21 (1H, t-like) MS TSP (m/z): 459 (M+H)$^+$ Example 38

3β,24(4β)-Isopropylidenedioxy-22β-tosyloxyolean-12-ene (compound 50)

Compound 1 (500 mg) was dissolved in pyridine, 287 mg of p-toluenesulfonyl chloride and a catalytic amount of 4-dimethylaminopyridine were added to the solution, and the mixture was stirred at room temperature overnight. Water was added to the reaction solution, the mixture was extracted with ethyl acetate, and the extract was dried over magnesium sulfate. The inorganic salt was removed by filtration, and the filtrate was concentrated under reduced pressure to give 654 mg (yield 100%) of compound 50 as a colorless solid.

$^1$H-NMR (CDCl$_3$) δppm 0.76 (3H, s), 0.84 (9H, s), 0.94 (3H, s), 0.96 (3H, s), 1.10 (3H, s), 1.14 (3H, s), 1.21 (3H, s), 1.37 (3H, s), 1.44 (3H, s), 0.78–2.10 (21H, m), 2.45 (3H, s), 3.22 (1H, d, J=11.65 Hz), 3.43–3.46 (1H, m), 4.03 (1H, d, J=11.65 Hz), 4.34–4.37 (1H, m), 5.22 (1H, t-like) MS FD (m/z): 652 (M$^+$)

Example 39

3β,24(4β)-Isopropylidenedioxyolean-12,21-diene (compound 51)

Triethylboronlithium hydride (1.0 M THF solution, 2 ml) was added to 65 mg of compound 50 under ice cooling, and the mixture was stirred at 65° C. for 1 hr. The temperature of the reaction solution was returned to room temperature. Water was added to the reaction solution, the mixture was extracted with ethyl acetate, and the extract was dried over magnesium sulfate. The inorganic salt was removed by filtration, and the filtrate was concentrated under reduced pressure to obtain a solid which was then purified by column chromatography on silica gel (development system, n-hexane:ethyl acetate=10:1) to give 38 mg (yield: 79%) of compound 51 as a colorless solid.

$^1$H-NMR (CDCl$_3$) δppm 0.88 (3H, s), 0.96 (9H, s), 0.98 (3H, s), 0.99 (3H, s), 1.12 (3H, s), 1.17 (3H, s), 1.22 (3H, s), 1.38 (3H, s), 1.44 (3H, s), 0.90–2.13 (19H, m), 3.23 (1H, d, J=11.54 Hz), 3.45–3.48 (1H, m), 4.05 (1H, d, J=11.54 Hz), 5.20–5.32 (3H, m) MS EI (m/z): 480 (M$^+$)

Example 40

Olean-12,21-diene-3β,24(4β)-diol (compound 52)

Compound 51 (48 mg) was dissolved in 1 ml of methanol and 1 ml of dichloromethane, 0.5 ml of 1 N hydrochloric acid was added to the solution, and the mixture was stirred for 1 hr. The reaction solution was diluted with dichloromethane, washed with water, and dried over magnesium sulfate. The inorganic salt was removed by filtration, and the filtrate was concentrated under reduced pressure to give 36 mg (yield: 82%) of compound 52 as a colorless solid.

$^1$H-NMR (CDCl$_3$) δppm 0.87 (3H, s), 0.90 (3H, s), 0.94 (3H, s), 0.95 (3H, s), 0.98 (3H, s), 1.11 (3H, s), 1.25 (3H, s), 0.84–2.13 (19H, m), 2.36 (1H, d, J=4.10 Hz), 2.68 (1H, d, J=6.67 Hz), 3.32–3.37 (1H, m), 3.43–3.48 (1H, m), 4.21 (1H, d, J=11.28 Hz), 5.20–5.30 (3H, m) MS EI (m/z): 440 (M$^+$)

Example 41

Olean-12-ene-3β,24(4β)-diol (compound 53)

Compound 51 (30 mg) was dissolved in 2 ml of methanol and 1 ml of dichloromethane, and 5 mg of 20% Pd(OH)$_2$—C was added to the solution. The mixture was catalytically reduced under atmospheric pressure overnight. The reaction solution was filtered, and the filtrate was concentrated under reduced pressure to give 26 mg (yield: 93%) of compound 53 as a colorless solid.

$^1$H-NMR (CDCl$_3$) δppm 0.82 (3H, s), 0.87 (6H, s), 0.89 (3H, s), 0.93 (3H, s), 1.13 (3H, s), 1.25 (3H, s), 1.25 (3H, s), 0.78–2.03 (23H, m), 2.37 (1H, d, J=4.16 Hz), 2.71 (1H, dd, J=2.50 Hz, 8.88 Hz), 3.32–3.37 (1H, m), 3.42–3.48 (1H, m), 4.21 (1H, d, J=10.88 Hz), 5.18 (1H, t-like) MS EI (m/z): 442 (M$^+$)

Example 42

3β-Benzoyloxyolean-12-en-24(4β)-ol (compound 56)

Compound 53 (1.00 g, 2.26 mmol) was dissolved in 10 ml of pyridine. Trityl chloride (881 mg, 3.16 mmol) was added to the solution, and the mixture was refluxed for 5 hr. The solvent was removed by distillation, water was added to the residue, the mixture was extracted with ethyl acetate, and the extract was dried over sodium sulfate. The inorganic salt was removed by filtration, and the filtrate was concentrated under reduced pressure to obtain 1.5 g of compound 54 (crude product). The compound 54 (crude product, 1.5 g) was dissolved in 20 ml of dichloromethane, 690 mg of 4-DMAP and 476.5 mg of benzoyl chloride were added to the solution, and the mixture was stirred for 2 hr. The reaction solution was diluted with dichloromethane, washed with water, and dried over sodium sulfate. The inorganic salt was removed by filtration, and the filtrate was concentrated under reduced pressure to give 1.7 g of compound 55 (crude product). The compound 55 (crude product, 1.7 g) was dissolved in 20 ml of methanol and 50 ml of acetone. Concentrated hydrochloric acid (0.5 ml) was added to the solution, and the mixture was stirred at 70° C. for 2 hr. The reaction solution was then neutralized with 1 N sodium hydroxide, and the solvent was removed by distillation. Water was added to the residue, the mixture was extracted with ethyl acetate, and the extract was dried over sodium sulfate. The inorganic salt was removed by filtration, and the filtrate was concentrated under reduced pressure to obtain a crude product which was then purified by column chromatography on silica gel (development system, n-hexane:ethyl acetate=10:1) to give 818 mg (yield: 66%) of compound 56 as a colorless solid.

$^1$H-NMR (CDCl$_3$) δppm 0.84 (3H, s), 0.87 (3H, s), 0.88 (3H, s), 0.98 (3H, s), 1.14 (3H, s), 1.15 (3H, s), 1.60 (3H, s), 0.80–2.10 (24H, m), 3.59 (1H, t, J=10.7 Hz), 4.26 (1H, dd, J=11.7 Hz, 2.6 Hz), 4.92 (1H, dd, J=8.6 Hz, 7.6 Hz), 5.19 (1H, t, J=3.6 Hz), 7.43–7.60 (3H, m), 7.96–8.00 (2H, m). FABMS (m/z): 569 (M$^+$+Na)

Example 43

3β-Benzoyloxy-24(4β)-oxolean-12-ene (compound 57)

Compound 56 (1.50 mg) was dissolved in 5 ml of dichloromethane, 71.1 mg of pyridinium chlorochromate was added to the solution, and the mixture was stirred for 1 hr. One hr after the initiation of stirring, 71.1 mg of pyridinium chlorochromate was added to the reaction solution, and the mixture was further stirred for 1 hr. Silica gel was added to the reaction solution, followed by filtration. The filtrate was concentrated under reduced pressure to obtain a crude product which was then purified by column chromatography on silica gel (development system, n-hexane:ethyl acetate=20:1) to give 142 mg (yield: 95%) of compound 57 as a colorless solid.

$^1$H-NMR (CDCl$_3$) δppm 0.83 (3H, s), 0.88 (3H, s), 0.91 (3H, s), 0.96 (3H, s), 1.16 (3H, s), 1.17 (3H, s), 1.58 (3H, s), 0.80–2.20 (23H, m), 4.93 (1H, dd, J=11.4 Hz, 5.9 Hz), 5.20 (1H, t, J=3.5 Hz), 7.41–7.59 (3H, m), 7.97–8.00 (2H, m), 10.23 (1H, s). FABMS (m/z): 545 (M$^+$+1)

Example 44

24(4β)-Oxolean-12-en-3β-ol (compound 58)

Compound 57 (121 mg, 0.222 mmol) was dissolved in 3 ml of methanol and 4 ml of THF, 0.5 ml of 1 N sodium hydroxide was added to the solution, and the mixture was stirred for 3 hr. The reaction solution was neutralized with 1 N hydrochloric acid, and the solvent was removed by distillation. Water was added to the residue, the mixture was extracted with ethyl acetate, and the extract was dried over sodium sulfate. The inorganic salt was removed by filtration, and the filtrate was concentrated under reduced pressure to obtain a crude product which was then purified by column chromatography on silica gel (development system, n-hexane:ethyl acetate=12:1) to give 75.4 mg (yield: 77%) of compound 58 as a colorless solid.

β$^1$H-NMR (CDCl$_3$) δppm 0.83 (3H, s), 0.87 (9H, s), 0.99 (3H, s), 1.14 (3H, s), 1.29 (3H, s), 0.80–2.10 (23H, m), 3.10–3.25 (2H, m), 5.19 (1H, t, J=3.6 Hz), 9.77 (1H, d, J=2.3 Hz). FABMS (m/z): 441 (M$^+$+1)

Example 45

24(4β)-Methylolean-12-ene-3β,24(4β)-diol (compound 59)

Compound 58 (50.0 mg, 0.114 mmol) was dissolved in 2 ml of THF, and the solution was cooled to −78° C. An ether solution of MeLi (0.42 ml, 1.08 mmol/ml) was added to the solution at the same temperature. The temperature of the mixture was gradually raised to 0° C. over a period of 30 min, followed by stirring at 0° C. for additional 10 min. Water was added to the reaction solution, the mixture was extracted with ethyl acetate, and the extract was dried over sodium sulfate. The inorganic salt was removed by filtration, and the filtrate was concentrated under reduced pressure to obtain a crude product which was then purified by preparative TLC (development system, n-hexane:THF=2.2:1) to give 39.0 mg (yield: 75%) of compound 59 as a colorless solid.

¹H-NMR (CDCl₃) δppm 0.83 (3H, s), 0.87 (6H, s), 0.96 (3H, s), 0.97 (3H, s), 1.12 (3H, s), 1.17 (3H, s), 1.23 (3H, d, J=6.3 Hz), 0.80–2.10 (25H, m), 3.42 (1H, dd, J=12.1 Hz, 3.8 Hz), 4.57 (1H, q, J=6.3 Hz), 5.19 (1H, t, J=3.6 Hz). FABMS (m/z): 479 (M⁺+Na)

Example 46

3β-Benzyloxyolean-12-en-24(4β)-oic acid (compound 60)

Compound 57 (300 mg) was dissolved in 15 ml of tert-butanol butanol, and 2.93 ml of 2-methyl-2-butene was added to the solution. A solution of 250 mg of sodium chlorite and 430 mg of monosodium phosphate in 2.0 ml of water was added to the mixture, and the mixture was then stirred at room temperature overnight. The reaction solution was concentrated under reduced pressure, the concentrate was extracted with ethyl acetate, and the extract was dried over sodium sulfate. The inorganic salt was removed by filtration, and the filtrate was concentrated under reduced pressure to obtain an oil which was then purified by column chromatography on silica gel (development system, n-hexane:ethyl acetate=4:1) to give 261 mg (yield: 85%) of compound 60 as a colorless solid.

¹H-NMR (CDCl₃) δppm 0.84 (3H, s), 0.87 (3H, s), 0.88 (3H, s), 1.00 (3H, s), 1.01 (3H, s), 1.16 (3H, s), 1.37 (3H, s), 0.80–2.60 (23H, m), 4.81 (1H, dd, J=12.3 Hz, 4.3 Hz), 5.21 (1H, t, J=3.4 Hz), 7.40–7.58 (3H, m), 8.05–8.08 (2H, m), FABMS (m/z): 583 (M⁺+Na)

Example 47

Methyl{olean-12-en-3β-ol-24(4β)-ate}(compound 62)

Compound 60 (251 mg) was dissolved in 1 ml of methanol and 6 ml of THF, 1 ml of 4 N sodium hydroxide was added to the solution, and the mixture was stirred at room temperature overnight. It was then adjusted to pH 3 by the addition of 1 N hydrochloric acid, and the solvent was removed by distillation. Water was added to the residue, the mixture was extracted with ethyl acetate, and the extract was dried over sodium sulfate. The inorganic salt was removed by filtration, and the filtrate was concentrated under reduced pressure to obtain a concentrate which was dissolved in 6 ml of methanol and 6 ml of THF. An excessive amount of a solution of trimethylsilyldiazomethane in hexane was added to the solution, and the mixture was stirred at room temperature for 1 min. The reaction solution was concentrated under reduced pressure to obtain a crude product which was then purified by column chromatography on silica gel (development system, n-hexane:ethyl acetate=15:1) to give 136 mg (yield: 65%) of compound 62 as a colorless solid.

¹H-NMR (CDCl₃) δppm 0.79 (3H, s), 0.83 (3H, s), 0.87 (3H, s), 0.98 (3H, s), 1.13 (3H, s), 1.41 (3H, s), 1.58 (3H, s), 0.80–2.10 (23H, m), 3.09 (1H, td, J=12.0 Hz, 4.5 Hz), 3.34–3.38 (1H, m), 3.68 (3H, s), 5.19 (1H, t, J=3.5 Hz). FABMS (m/z): 493 (M⁺+Na)

Example 48

24(4β)-Methyl-24(4β)oxolean-12-en-3β-ol (compound 63) and

24(4β),24(4β)-Dimethylolean-12-ene-3β,24(4β)-diol (compound 64)

Compound 62 (30.0 mg) was dissolved in 2 ml of THF, and the solution was cooled to −78° C. An ether solution of MeLi (0.71 ml, 1.08 mmol/ml) was added to the solution at the same temperature. The temperature of the mixture was gradually raised to room temperature over a period of 30 min, and the mixture was stirred at room temperature for 4 hr. Water was added to the reaction solution, the mixture was extracted with ethyl acetate, and the extract was dried over sodium sulfate. The inorganic salt was removed by filtration, and the filtrate was concentrated under reduced pressure to obtain a crude product which was then purified by preparative TLC (development system, n-hexane:THF=6:1) to give 16.7 mg (yield: 58%) of compound 63 and 3.4 mg (yield: 11%) of compound 64 as a colorless solid.

¹H-NMR (CDCl₃) δppm (compound 63) 0.81 (3H, s), 0.83 (3H, s), 0.87 (3H, s), 1.01 (3H, s), 1.14 (3H, s), 1.39 (3H, s), 1.59 (3H, s), 2.18 (3H, s), 0.80–2.20 (23H, m), 3.05 (1H, td, J=11.9 Hz, 4.1 Hz), 3.18–3.22 (1H, m), 5.20 (1H, t, J=3.6 Hz). FABMS (m/z): 454 (M⁺+1)

¹H-NMR (CDCl₃) δppm (compound 64) 0.83 (3H, s), 0.87 (6H, s), 1.02 (3H, s), 1.12 (3H, s), 1.19 (3H, s), 1.22 (3H, s), 1.41 (3H, s), 1.42 (3H, s), 0.80–2.40 (25H, m), 3.37–3.43 (1H, m), 5.21 (1H, t, J=3.6 Hz). FABMS (m/z): 493 (M⁺+Na)

Example 49

22-Methyleneolean-12-en-3-ol (compound 65)

Compound 58 (25 mg) was dissolved in 1 ml of THF, 0.57 ml of 0.5 mmol/ml solution of the Tebbe reagent in toluene was added to the solution at 0° C., and the mixture was stirred at 0° C. for 30 min and then at room temperature overnight. Diethyl ether and 1 N NaOH were added to the reaction solution, followed by filtration. The filtrate was concentrated under reduced pressure. Water was added to the concentrate, the mixture was extracted with ethyl acetate, and the extract was then dried over sodium sulfate. The inorganic salt was removed by filtration, and the filtrate was concentrated under reduced pressure to obtain a crude product which was then purified by preparative TLC (development system, n-hexane:THF=5:1) to give 17.9 mg (yield: 72%) of compound 65 as a colorless solid.

¹H-NMR (CDCl₃) δppm 0.83 (3H, s), 0.87 (6H, s), 0.93 (3H, s), 0.94 (3H, s), 1.14 (3H, s), 1.18 (3H, s), 0.80–2.10 (24H, m), 3.20–3.35 (1H, m), 5.09 (1H, dd, J=17.6 Hz, 1.7 Hz), 5.17–5.24 (2H, m), 6.06 (1H, dd, J=17.6 Hz, 11.2 Hz). FABMS (m/z): (M⁺+Na)

Example 50

21-Oxolean-12-en-3β,24(4β)-diol (compound 66)

Compound 66 (6 mg, yield: 100%) was prepared from 7 mg of compound 47 in the same manner as in Example 19.

¹H-NMR (CDCl₃) δppm 0.89 (3H, s), 0.93 (3H, s), 0.94 (3H, s), 1.00 (6H, s), 1.11 (3H, s), 1.20 (3H, s), 1.25 (3H, s), 0.83–2.50 (23H, m), 3.34 (1H, d, J=11.0 Hz), 3.45 (1H, dd, J=3.8 Hz, 11.0 Hz), 4.21 (1H, d, J=11.0 Hz), 5.32 (1H, t-like) MS TSP (m/z):474 (M⁺NH₄⁺)

Example 51

22β-Ethylmalonyloxy-3β,24(4β)-isopropylidenedioxyolean-12-ene (compound 67)

Compound 3 (100 mg) was dissolved in 3 ml of dichloromethane, 37 mg of 4-dimethylaminopyridine and 38 μl of ethylmalonyl chloride were added to the solution, and the mixture was stirred at room temperature for 30 min. A saturated sodium hydrogencarbonate solution was added to the reaction solution, and the reaction solution was extracted twice with dichloromethane. The organic layer was washed with saturated saline and dried over magnesium sulfate. The inorganic salt was removed by filtration, and the filtrate was concentrated under reduced pressure to obtain a concentrate which was then purified by column chromatography on silica gel (development system, n-hexane:ethyl acetate=5:1) to give 85 mg (yield: 67%) of compound 67 as a colorless solid.

$^1$H-NMR (CDCl$_3$) δppm 0.83 (3H, s), 0.90 (3H, s), 0.98 (3H, s), 0.99 (3H, s), 1.15 (3H, s), 1.16 (3H, s), 1.22 (3H, s), 1.28 (3H, t, J=7.2 Hz), 1.38 (3H, s), 1.44 (3H, s), 0.86–2.21 (21H, m), 3.23 (1H, d, J=11.5 Hz), 3.35 (2H, s), 3.46 (1H, dd, J=4.6 Hz, 9.5 Hz), 4.05 (1H, d, J=11.5 Hz), 4.19 (2H, q, J=7.2 Hz), 4.73 (1H, t-like), 5.32 (1H, t-like) MS TSP (m/z): 635 (M+Na$^+$)

Example 52

22β-Malonyloxyolean-12-ene-3β,24(4β)-diol (compound 68)

Compound 67 (73 mg) was dissolved in 5 ml of ethanol and 1 ml of dichloromethane, 0.8 ml of 1 N sodium hydroxide was added to the solution, and the mixture was stirred at room temperature for 1 hr. The reaction solution was acidified with 1 N hydrochloric acid and extracted with dichloromethane. The extract was concentrated under reduced pressure. The concentrate was dissolved in 2 ml of methanol and 1 ml of dichloromethane, 0.5 ml of 1 N hydrochloric acid was added to the mixture, and the mixture was stirred at room temperature for 30 min. Water was added to the reaction solution, the mixture was extracted with dichloromethane, and the extract was then dried over magnesium sulfate. The inorganic salt was removed by filtration, and the filtrate was concentrated under reduced pressure to give 54 mg (yield: 83%) of compound 68 as a colorless solid.

$^1$H-NMR (CDCl$_3$+CD$_3$OD) δppm 0.81 (3H, s), 0.87 (3H, s), 0.88 (3H, s), 0.91 (3H, s), 0.96 (3H, s), 1.12 (3H, s), 1.22 (3H, s), 0.84–2.20 (21H, m), 3.28–3.44 (2H, m), 3.33 (2H, s), 4.18 (1H, d, J=11.3 Hz), 4.71 (1H, t-like), 5.22 (1H, t-like) MS FAB (m/z): 567 (M+Na$^+$)

Example 53

3β,24(4β)-Isopropylidenedioxy-22β-methoxycarbonylpropoxyolean-12-ene (compound 69)

Compound 3 (50 mg) was dissolved in 1 ml of anhydrous DMF, 20 mg of 60% sodium hydride was added to the solution, and the mixture was stirred at room temperature for 2.5 hr. Thereafter, 87 μl of trimethyl 4-bromoorthobutyrate was added to the reaction solution, and the mixture was stirred at 50° C. overnight. Ethyl acetate was added to the reaction solution, and the mixture was washed twice with water, and dried over magnesium sulfate. The inorganic salt was removed by filtration, and the filtrate was concentrated under reduced pressure to obtain a concentrate which was then purified by column chromatography on silica gel (development system, n-hexane:ethyl acetate=5:1) to give 15 mg (yield: 24%) of compound 69 as a colorless solid.

$^1$H-NMR (CDCl$_3$) δppm 0.86 (3H, s), 0.88 (3H, s), 0.99 (3H, s), 1.00 (3H, s), 1.12 (3H, s), 1.16 (3H, s), 1.22 (3H, s), 1.38 (3H, s), 1.44 (3H, s), 0.82–2.13 (23H, m), 2.43 (2H, t, J=7.2 Hz), 2.86–2.89 (1H, m), 3.16–3.22 (1H, m), 3.23 (1H, d, J=11.5 Hz), 3.46 (1H, dd, J=4.6 Hz, 9.5 Hz), 3.52–3.58 (1H, m), 3.67 (3H, s), 4.05 (1H, d, J=11.5 Hz), 5.23 (1H, t-like) MS TSP (m/z): 599 (M+H)$^+$

Example 54

22β-Methoxycarbonylpropoxyolean-12-ene-3β,24(4β)-diol (compound 70)

Compound 69 (15 mg) was dissolved in 1 ml of methanol and 0.5 ml of dichloromethane, 0.2 ml of 1 N hydrochloric acid was added to the solution, and the mixture was stirred at room temperature for 15 min. The reaction solution was extracted with dichloromethane, and the extract was dried over magnesium sulfate. The inorganic salt was removed by filtration, and the filtrate was concentrated under reduced pressure to give 13 mg (yield: 94%) of compound 70 as a colorless solid.

$^1$H-NMR (CDCl$_3$) δppm 0.86 (3H, s), 0.87 (3H, s), 0.89 (3H, s), 0.94 (3H, s), 1.00 (3H, s), 1.11 (3H, s), 1.25 (3H, s), 0.83–2.13 (25H, m), 2.42 (2H, t, J=7.2 Hz), 2.86–2.88 (1H, m), 3.16–3.22 (1H, m), 3.32–3.38 (1H, m), 3.42–3.48 (1H, m), 3.52–3.58 (1H, m), 3.67 (3H, s), 4.21 (1H, d, J=11.0 Hz), 5.21 (1H, t-like) MS TSP (m/z): 576 (M+NH$_4^+$)

Example 55

Olean-12-ene-3β,24(4β)-diol-22β-O-propanecarboxylic acid (compound 71)

Compound 70 (13 mg) was dissolved in 2 ml of methanol and 1 ml of dichloromethane, 0.8 ml of 1 N sodium hydroxide was added to the solution, and the mixture was stirred at room temperature for 10 hr. The reaction solution was acidified with 1 N hydrochloric acid and extracted with dichloromethane, and the extract was dried over magnesium sulfate. The inorganic salt was removed by filtration, and the filtrate was concentrated under reduced pressure to give 10 mg (yield: 83%) of compound 71 as a colorless solid.

$^1$H-NMR (CDCl$_3$+CD$_3$OD) δppm 0.86 (3H, s), 0.88 (3H, s), 0.89 (3H, s), 0.94 (3H, s), 1.00 (3H, s), 1.11 (3H, s), 1.24 (3H, s), 0.82–2.12 (23H, m), 2.43 (2H, t, J=7.2 Hz), 2.88–2.91 (1H, m), 3.20–3.26 (1H, m), 3.33 (1H, d, J=11.0 Hz), 3.39–3.44 (1H, m), 3.53–3.60 (1H, m), 4.20 (1H, m), 5.22 (1H, t-like) MS TSP (m/z): 543 (M−H)$^-$

Example 56

3β,24(4β)-Isopropylidenedioxy-22β-anilinecarbonyloxyolean-12-ene (compound 72)

Compound 3 (30.0 mg) was dissolved in 2 ml of pyridine, 14 mg of phenyl isocyanate was added to the solution, and the mixture was refluxed for 1 hr. Water was added to the reaction solution, the mixture was extracted with ethyl acetate, and the extract was dried over sodium sulfate. The inorganic salt was removed by filtration, and the filtrate was concentrated under reduced pressure to obtain a solid which was then purified by preparative TLC (development system, n-hexane:THF=7:1) to give 23.0 mg (yield: 62%) of compound 72 as a colorless solid.

$^1$H-NMR (CDCl$_3$) δppm 0.89 (3H, s), 0.92 (3H, s), 1.00 (3H, s), 1.02 (3H, s), 1.16 (6H, s), 1.23 (3H, s), 1.38 (3H, s), 1.44 (3H, s), 0.80–2.30 (21H, m), 3.23 (1H, d, J=11.6 Hz), 3.46 (1H, dd, J=9.3, 4.1 Hz), 4.05 (1H, d, J=11.6 Hz), 4.65 (1H, t, J=3.8 Hz), 5.27 (1H, t-like), 6.50 (1H, s), 7.05 (1H, t, J=7.2 Hz), 7.28–7.42 (4H, m). FABMS (m/z): 640 (M+Na)$^+$

Example 57

22β-Anilinocarbonyloxyolean-12-ene-3β,24(4β)-diol (compound 73)

Compound 72 (20.0 mg) was dissolved in 1 ml of methanol, 0.1 ml of 1 N HCl was added to the solution, and the mixture was stirred at room temperature for 5 min. The solvent was removed by distillation, a saturated NaHCO$_3$ solution was added to the residue, and the mixture was extracted with ethyl acetate. The extract was dried over sodium sulfate. The inorganic salt was removed by filtration, and the filtrate was concentrated under reduced pressure to obtain a solid which was then purified by preparative TLC (development system, n-hexane:THF=2.5:1) to give 16.2 mg (yield: 87%) of compound 73 as a colorless solid.

$^1$H-NMR (CDCl$_3$) δppm 0.88 (3H, s), 0.90 (3H, s), 0.92 (3H, s), 0.95 (3H, s), 1.02 (3H, s), 1.15 (3H, s), 1.25 (3H, s), 0.80–2.70 (23H, m), 3.31–3.49 (2H, m), 4.21 (1H, dd, J=11.4, 2.0 Hz), 4.65 (1H, t, J=4.1 Hz), 5.26 (1H, t, J=3.2 Hz), 6.49 (1H, s), 7.05 (1H, t, J=7.4 Hz), 7.27–7.43 (4H, m). FABMS (m/z): 600 (M+Na)$^+$ Example 58

22β-Aminocarbonyloxyolean-12-ene-3β,24(4β)-diol (compound 74)

Compound 3 (5.6 mg) was dissolved in 0.2 ml of pyridine, 4.2 mg of trichloroacetyl isocyanate was added to the solution, and the mixture was stirred at room temperature for 1 hr. The reaction solution was concentrated under reduced pressure to obtain a solid. Methanol (0.5 ml) and 6.2 mg of potassium carbonate were added to the solid, and the mixture was stirred at room temperature for 10 min. The solvent was removed by distillation, water was added to the residue, and the mixture was extracted with ethyl acetate. The extract was dried over sodium sulfate. The inorganic salt was removed by filtration, and the filtrate was concentrated under reduced pressure to obtain a solid which was then purified by preparative TLC (development system, n-hexane:AcOEt=1:1.5) to give 2.5 mg (yield: 44%) of compound 74 as a colorless solid.

$^1$H-NMR (CDCl$_3$) δppm 0.84 (3H, s), 0.89 (3H, s), 0.90 (3H, s), 0.95 (3H, s), 1.00 (3H, s), 1.14 (3H, s), 1.25 (3H, s), 0.80–2.80 (23H, m), 3.32–3.48 (2H, m), 4.21 (1H, d, J=11.0 Hz), 4.48–4.56 (3H, m), 5.24 (1H, t, J=3.5 Hz) FABMS (m/z): 524 (M+Na)$^+$ Preparation Example 1 Tablets The compound of the present invention was granulated by the wet process, magnesium stearate was added thereto, and the mixture was compressed to prepare tablets. Each tablet had the following composition.

| | |
|---|---|
| Compound 2 | 200 mg |
| Lactose | 50 mg |
| Carboxymethyl starch sodium | 20 mg |
| Hydroxypropylmethyl cellulose | 5 mg |
| Magnesium stearate | 3 mg |
| Total | 278 mg |

Preparation Example 2 Suppositories

Weilapzole H-15 was heated at 60° C., the compound 2 was added to and dispersed in the resultant melt, and the dispersion was filled into suppository containers. The suppository containers filled with the dispersion were cooled to room temperature to prepare suppositories. Each suppository had the following composition.

| | |
|---|---|
| Compound 2 | 200 mg |
| Weilapzole H-15 | 1000 mg |
| Total | 1200 mg |

Test Example 1

Effect in Hepatocytotoxicity Inhibitory Model (in vitro)

A test compound was added to a concentration of 0.1 to 10 μg/ml to Hep G2 cells in the presence of aflatoxin B$_1$ (10$^{-5}$ M), and the cells were then incubated in a CO$_2$ incubator at 37° C. for 48 hr. After the completion of the incubation, the cells were dyed with trypan blue, and the dye incorporation capacity thereof was measured with Monocellater (manufactured by Olympus Optical Co., Ltd.). The hepatocytotoxicity inhibitory activity (%) was calculated according to the following equation. In the equation, the value of the control group is the absorbance (%) in the presence of aflatoxin B$_1$ alone, and the value of the treated group is the absorbance (%) in the copresence of aflatoxin B$_1$ and the test compound.

As a result, the hepatocytotoxicity inhibitory activity of the compounds 2, 6, 10, 17, 20, 22, 26, 27, 32, 33, 36, 37, 46, 49, 66, and 73 was not less than 5%.

$$\text{Hepatocytotoxicity inhibitory avtivity}(\%) = \frac{\text{value of control group} - \text{value of treated group}}{100 - \text{value of control group}} \times 100$$

Test Example 2

Effect in Concanavalin A (Con A) Hepatitis Model

Con A dissolved in physiological saline was intravenously administered at a dose of 20 mg/kg to BALB/c male mice (8 weeks in age) having a body weight of 21 to 25 g to induce hepatitis. A test compound (compound 7) was suspended in a mixed solution (control vehicle) composed of 25% dimethylsufoxide, 25% polyethylene glycol 400, and 0.25% carboxymethyl cellulose, and the suspension was subcutaneously administered 2 hr and 14 hr before the administration of Con A at three levels of dose, i.e., 0.2 mg/mouse, 1.0 mg/mouse, and 2.0 mg/mouse. A control vehicle alone was administered to a group of control mice. Twenty four hr after the administration of Con A, the mice were sacrificed under ether anesthesia to assay the alanine aminotransferase (ALT) activity, in plasma, as an index of hepatopathy.

The results were as shown in FIG. 1. Specifically, the ALT activity was 2068±518 (u/l) for the group of mice which had not been treated with the test compound (control group), whereas the ALT activity was lowered to the same level as that for the group of mice which had not been treated with Con A (that is, normal value), that is, 55±16 (u/l) for the group of mice which had been treated with the compound 7 at a dose of 1.0 mg/mouse and the group of mice which had been treated with the compound 7 at a dose of 2.0 mg/mouse.

What is claimed is:

1. A method for treating a hepatic disorder, wherein the hepatic disorder is selected from the group consisting of chronic viral hepatitis, autoimmune hepatitis, and drug-induced, toxic, alcoholic, intrahepatic cholestasis, and inborn metabolic error hepatopathy, comprising administering to an animal a triterpene derivative represented by the following formula (II) or a salt thereof:

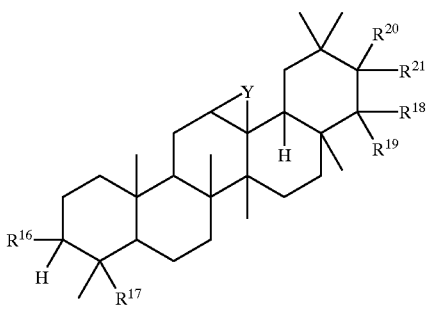

(II)

wherein
$R^{16}$ represents
a hydroxyl group,
arylmethyloxy,
lower alkoxy, or
lower alkanoyloxy;
$R^{17}$ represents
lower alkyl,
lower alkenyl,
—$CH_2OR^5$ wherein $R^5$ represents a hydrogen atom, arylmethyl, lower alkyl, or lower alkanoyl,
formyl,
—$COOR^6$ wherein $R^6$ represents a hydrogen atom or lower alkyl,
—$CH_2OCON(R^9)R^{10}$ wherein $R^9$ and $R^{10}$, which may be the same or different, represent a hydrogen atom, lower alkyl, or aryl,
—$CON(R^{29})R^{30}$ wherein $R^{29}$ and $R^{30}$, which may be the same or different, represent a hydrogen atom, lower alkyl, lower alkanoyl, aryl, or aralkyl;
—$CH_2N(R^7)R^8$ wherein $R^7$ and $R^8$, which may be the same or different, represent a hydrogen atom, lower alkyl, aryl, or lower alkanoyl;
—$C(R^6)_2OH$ wherein $R^6$ is as defined above;
—$COR^{6a}$ wherein $R^{6a}$ represents lower alkyl;
—$CH$=$CHR^6$ wherein $R^6$ is as defined above;
or $R^{16}$ and $R^{17}$ may combine with each other to form —O—$C(R^9)R^{10}$—O—$CH_2$— wherein $R^9$ and $R^{10}$ are as defined above;
$R^{18}$ and $R^{19}$, which may be the same or different, represent
a hydrogen atom,
a hydroxyl group,
arylmethyloxy,
—$N(R^{11})R^{12}$ wherein $R^{11}$ and $R^{12}$ which may be the same or different, represent a hydrogen atom, lower alkyl, or lower alkanoyl,
—$COOR^6$ wherein $R^6$ is as defined above,
—$OR^{13}$ wherein $R^{13}$ represents lower alkyl, cyclo-lower alkyl, aralkyl, lower alkanoyl, arylcarbonyl, aralkylcarbonyl, lower alkenyl, lower alkenylcarbonyl, or aryl-lower alkenylcarbonyl,
—O—$(CH_2)_m$—$R^{22}$ wherein
$R^{22}$ represents
amino,
—NH—$COOR^{23}$ wherein $R^{23}$ represents arylmethyl or lower alkyl,
a hydroxyl group,
arylmethyloxy, or
—$COOR^{24}$ wherein $R^{24}$ represents a hydrogen atom, lower alkyl, or arylmethyl, and
m is an integer of 1 to 4,
—$OCOCH(R^{25})(CH_2)_n$—$R^{22}$ wherein $R^{22}$ is as defined above, $R^{25}$ represents a hydrogen atom, lower alkyl, aralkyl, or aryl, and n is an integer of 0 to 3,
—$OCOCH$=$CH$—$COOR^6$ wherein $R^6$ is as defined above, or —$OCON(R^{29})R^{30}$ wherein $R^{29}$ and $R^{30}$ are as defined above;
or $R^{18}$ and $R^{19}$ may combine with each other to form oxo,
$R^{20}$ and $R^{21}$ respectively represent the same meanings as $R^{18}$ and $R^{19}$, provided that $R^{20}$ and $R^{21}$ do not represent a hydrogen atom at the same time;
or $R^{18}$ and $R^{20}$ may combine with each other to form —O—$[C(R^9)R^{10}]_p$—O— wherein $R^9$ and $R^{10}$ are as defined above and p is an integer of 1 to 3, or —OCO—$[C(R^9)R^{10}]_q$—OCO— wherein $R^9$ and $R^{10}$ are as defined above and q is an integer of 0 to 2; and
Y represents O, $CH_2$, NH, or a single bond to form a double bond in the ring with Y bonded thereto.

2. The method according to claim 1, wherein $R^{16}$ represents a hydroxyl group, $R^{17}$ represents —$CH_2OH$, both $R^{18}$ and $R^{20}$ represent a hydrogen atom, both $R^{19}$ and $R^{21}$ represent a hydroxyl group and Y represents a single bond to form a double bond in the ring with Y bonded thereto.

3. The method according to claim 1, wherein $R^{16}$ represents a hydroxyl group, lower alkoxy, or lower alkanoyloxy, $R^{17}$ represents —$CH_2OR^5$, $R^{18}$ represents a hydrogen atom, $R^{19}$ represents —$OR^{13}$, $R^{20}$ represents a hydrogen atom, $R^{21}$ represents —$OR^{13}$ and Y represents a single bond to form a double bond in the ring with Y bonded thereto.

4. The method according to claim 1, wherein $R^{16}$ represents a hydroxyl group, lower alkoxy, or lower alkanoyloxy, $R^{17}$ represents —$CH_2OR^5$, $R^{18}$ and $R^{19}$ represent a hydrogen atom, $R^{20}$ represents a hydrogen atom, $R^{21}$ represents a hydroxyl group and Y represents a single bond to form a double bond in the ring with Y bonded thereto.

5. The method according to claim 1, wherein $R^{16}$ represents a hydroxyl group, $R^{17}$ represents —$CH_2OR^5$, $R^{18}$ represents a hydrogen atom, $R^{19}$ represents a hydroxyl group or —$OR^{13}$, $R^{20}$ represents a hydrogen atom, $R^{21}$ represents a hydroxyl group or —$OR^{13}$ and Y represents O.

6. The method according to claim 1, wherein $R^{16}$ represents a hydroxyl group, lower alkoxy, or lower alkanoyloxy, $R^{17}$ represents —$C(R^6)_2OH$, $R^{18}$ represents a hydrogen atom, $R^{19}$ represents a hydroxyl group or —$OR^{13}$, $R^{20}$ represents a hydrogen atom, $R^{21}$ represents a hydroxyl group or —$OR^{13}$ and Y represents a single bond to form a double bond in the ring with Y bonded thereto.

7. The method according to claim 1, wherein said animal is a human being.

* * * * *